United States Patent [19]
Stevens et al.

[11] Patent Number: 6,152,141
[45] Date of Patent: *Nov. 28, 2000

[54] METHOD FOR DELIVERY OF THERAPEUTIC AGENTS TO THE HEART

[75] Inventors: John H. Stevens, Palo Alto; Richard B. Brewer, Hillsborough; Daniel C. Rosenman, San Francisco; Hanson S. Gifford, III, Woodside, all of Calif.

[73] Assignee: Heartport, Inc., Redwood City, Calif.

[ * ] Notice: This patent is subject to a terminal disclaimer.

[21] Appl. No.: 08/986,917

[22] Filed: Dec. 8, 1997

Related U.S. Application Data

[60] Continuation-in-part of application No. 08/453,426, May 30, 1995, Pat. No. 5,885,238, which is a division of application No. 08/282,192, Jul. 28, 1994, Pat. No. 5,584,803, which is a continuation-in-part of application No. 08/650,112, May 22, 1996, Pat. No. 6,029,671, which is a division of application No. 08/415,355, Mar. 31, 1995, abandoned.

[51] Int. Cl.[7] .................................................. A61B 19/00
[52] U.S. Cl. .................................. 128/898; 604/4; 604/96
[58] Field of Search ............................ 128/898; 604/4–6, 604/500, 101, 102, 280, 95, 69; 606/16, 17, 18

[56] References Cited

U.S. PATENT DOCUMENTS

| Re. 35,352 | 10/1996 | Peters . |
|---|---|---|
| 5,194,596 | 3/1993 | Tischer et al. . |
| 5,219,739 | 6/1993 | Tischer et al. . |
| 5,272,263 | 12/1993 | Hession et al. . |
| 5,279,565 | 1/1994 | Klein et al. . |
| 5,298,487 | 3/1994 | Chen et al. . |
| 5,312,344 | 5/1994 | Grinfeld et al. . |
| 5,318,957 | 6/1994 | Cid et al. . |
| 5,330,498 | 7/1994 | Hill . |
| 5,332,671 | 7/1994 | Ferrara et al. . |
| 5,336,178 | 8/1994 | Kaplan et al. . |
| 5,336,518 | 8/1994 | Narayanan et al. . |

(List continued on next page.)

FOREIGN PATENT DOCUMENTS

| 0218275 | 4/1987 | European Pat. Off. . |
|---|---|---|
| WO 97/47253 | 12/1997 | WIPO . |
| WO 98/05307 | 2/1998 | WIPO . |

OTHER PUBLICATIONS

Brown et al., "Enhancement of Wound Healing by Topical Treatment with Epidermal Growth Factor," *The New England Journal of Medicine*, 1989;321(2):76–79.

Burkhoff et al., "Histologic Appearance of Transmyocardial Laser Channels After 4½ Weeks," *Ann Thorac Surg*, 1996;61:1532–1535.

(List continued on next page.)

*Primary Examiner*—V. Millin
*Assistant Examiner*—Kelly O'Hara
*Attorney, Agent, or Firm*—Jens E. Hoekendijk; Michael J. Lynch

[57] ABSTRACT

A method for delivering a therapeutic agent directly to the heart employing minimally invasive techniques and concepts. In particular, the delivery of vascular endothelial growth factors (VEGF) is performed endovascularly or endoscopically to a region of a patient's heart treated with transmyocardial revascularization (TMR). A system is provided for inducing cardioplegic arrest. An aortic occlusion device has an inflatable balloon which occludes the ascending aorta when inflated. Cardioplegic fluid may be infused through a lumen of the aortic occlusion device to stop the heart while the patient's circulatory system is supported on cardiopulmonary bypass. A side-firing fiberoptic laser is introduced through the aortic occlusion device in the endovascular technique to perform TMR. Subsequently, a therapeutic agent delivery catheter is directed into one of the coronary arteries to deliver and dissipate the VEGF into the surrounding vascular plexus to promote angiogenesis stimulation. Alternatively, a therapeutic agent delivery material saturated or coated with VEGF could be sutured to the epicardial surface of the heart, using thoracoscopic techniques, for timed release delivery of the agent to the TMR treated site.

9 Claims, 15 Drawing Sheets

U.S. PATENT DOCUMENTS

| | | |
|---|---|---|
| 5,354,279 | 10/1994 | Hofling . |
| 5,370,685 | 12/1994 | Stevens . |
| 5,419,777 | 5/1995 | Hofling . |
| 5,425,705 | 6/1995 | Evard et al. . |
| 5,433,700 | 7/1995 | Peters .......................................... 604/4 |
| 5,452,733 | 9/1995 | Sterman et al. . |
| 5,458,574 | 10/1995 | Machold et al. . |
| 5,478,309 | 12/1995 | Sweezer et al. . |
| 5,499,996 | 3/1996 | Hill . |
| 5,501,698 | 3/1996 | Roth et al. . |
| 5,505,701 | 4/1996 | Anaya Fernandez de Lomana . |
| 5,522,838 | 6/1996 | Hill . |
| 5,533,516 | 7/1996 | Sahatjian . |
| 5,536,251 | 7/1996 | Evard et al. . |
| 5,545,214 | 8/1996 | Stevens . |
| 5,549,674 | 8/1996 | Humes et al. . |
| 5,556,412 | 9/1996 | Hill . |
| 5,558,644 | 9/1996 | Boyd et al. . |
| 5,567,417 | 10/1996 | Sasisekharan et al. . |
| 5,569,274 | 10/1996 | Rapacki et al. . |
| 5,571,215 | 11/1996 | Sterman et al. . |
| 5,575,815 | 11/1996 | Slepian et al. . |
| 5,580,722 | 12/1996 | Foulkes et al. . |
| 5,584,803 | 12/1996 | Stevens et al. . |
| 5,586,982 | 12/1996 | Abela . |
| 5,588,962 | 12/1996 | Nicholas et al. . |
| 5,591,197 | 1/1997 | Orth et al. . |
| 5,599,306 | 2/1997 | Klein et al. . |
| 5,618,307 | 4/1997 | Donlon et al. . |
| 5,626,607 | 5/1997 | Malecki et al. . |
| 5,634,895 | 6/1997 | Igo et al. . |
| 5,682,906 | 11/1997 | Sterman et al. . |
| 5,695,457 | 12/1997 | St. Goar et al. . |
| 5,702,368 | 12/1997 | Stevens et al. . |
| 5,718,725 | 2/1998 | Sterman et al. . |
| 5,885,238 | 3/1999 | Stevens et al. ............................. 604/4 |

OTHER PUBLICATIONS

Cooley et al., "Transmyocardial Laser Revascularization: Clinical Experience with Twelve–month Follow–up," *J Thorac Card Surg*, 1996;111(4):791–799.

Engler, "Use of Vascular Endothelial Growth Factor Angiogenesis," *Circulation*, 1996;94(7):1496–1498.

Fasol et al., "Experimental Use of a Modified Fibrin Glue to Induce Site–directed Angiogenesis from the Aorta to the Heart," *J Thorac Card Surg*, 1994;107(6):1432–1439.

Fleischer et al., "One–month Histologic Response of Transmyocardial Laser Channels with Molecular Intervention," *Ann Thorac Surg*, 1996;62:1051–1058.

Folkman and Klagsbrun, "Angiogenic Factors," *Science*, 1987;235:442–447.

Hockel et al., "Therapeutic Angiogenesis," *Arch Surg*, 1993;128:423–429.

Horvath et al., "Transmyocardial Laser Revascularization: Operative Techniques and Clinical Results at Two Years," *J Thorac Card Surg*, 1996;111(5):1047–1053.

Isner et al., "Arterial Gene Therapy for Therapeutic Angiogenesis in Patients with Peripheral Artery Disease," *Circulation*, 1995;91(11):2687–2692.

Kissel et al., "Parental Depot–systems on the Basis of Biodegradable Polyesters," *Journal of Controlled Substances*, 1991;16:27–41.

Langer, "New Methods of Drug Delivery," *Science*, 1990;249:1527–1533.

Langer and Moses, "Biocompatible Controlled Release Polymers for Delivery of Polypeptides and Growth Factors," *Journal of Cellular Biochemistry*, 1991;45:340–345.

Kohmoto et al., "Does Blood Flow Through Holmium; YAG Transmyocardial Laser Channels?" *Ann Thorac Surg*, 1996;61:861–868.

Rawlins, "Adverse Effects of Novel Delivery Systems," *Novel Drug Delivery and Its Theapeutic Application*, Chapter 22, pp. 237–243.

Smith et al., Transmyocardial Laser Revasculariztion, *J Card Surg*, 1995;10:569–572.

Tice et al., "Clinical Use and Future of Parental Microsphere Delivery Systems," *Novel Drug Delivery and It's Therapeutic Application*, Chapter 21, pp. 223–235.

Weatherford et al., "Vascular Endothelial Growth Factor and Heparin in a Biologic Glue Promotes Human Aortic Endothelial Cell Proliferation with Aortic Smooth Muscle Cell Inhibition," *Surgery*, 1996;120(2):433–439.

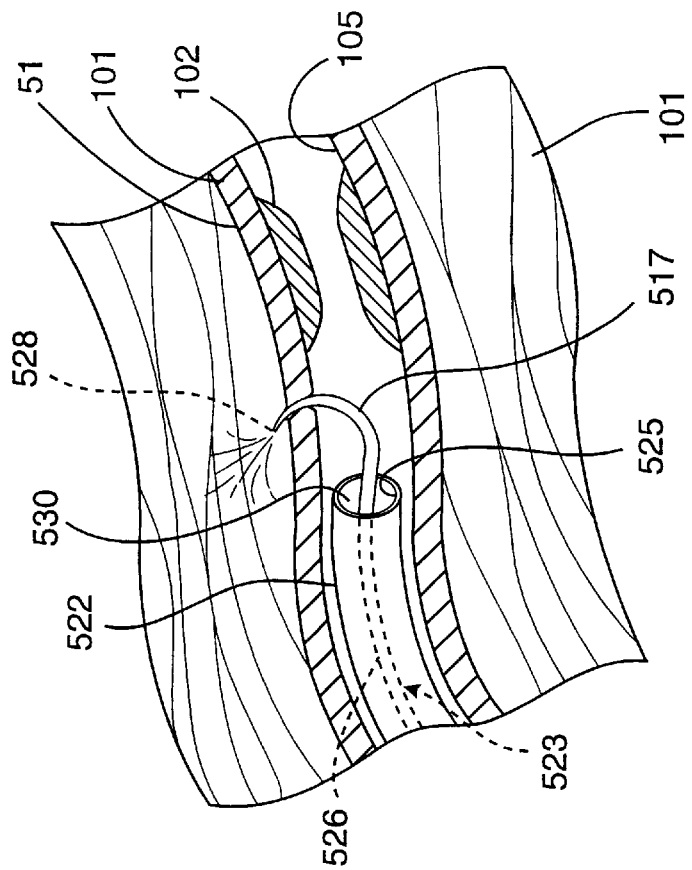
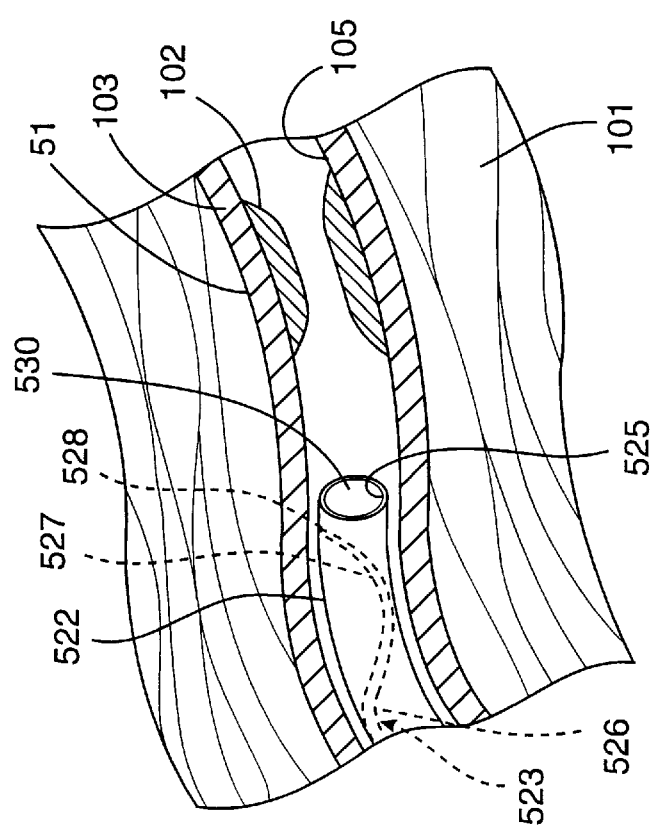

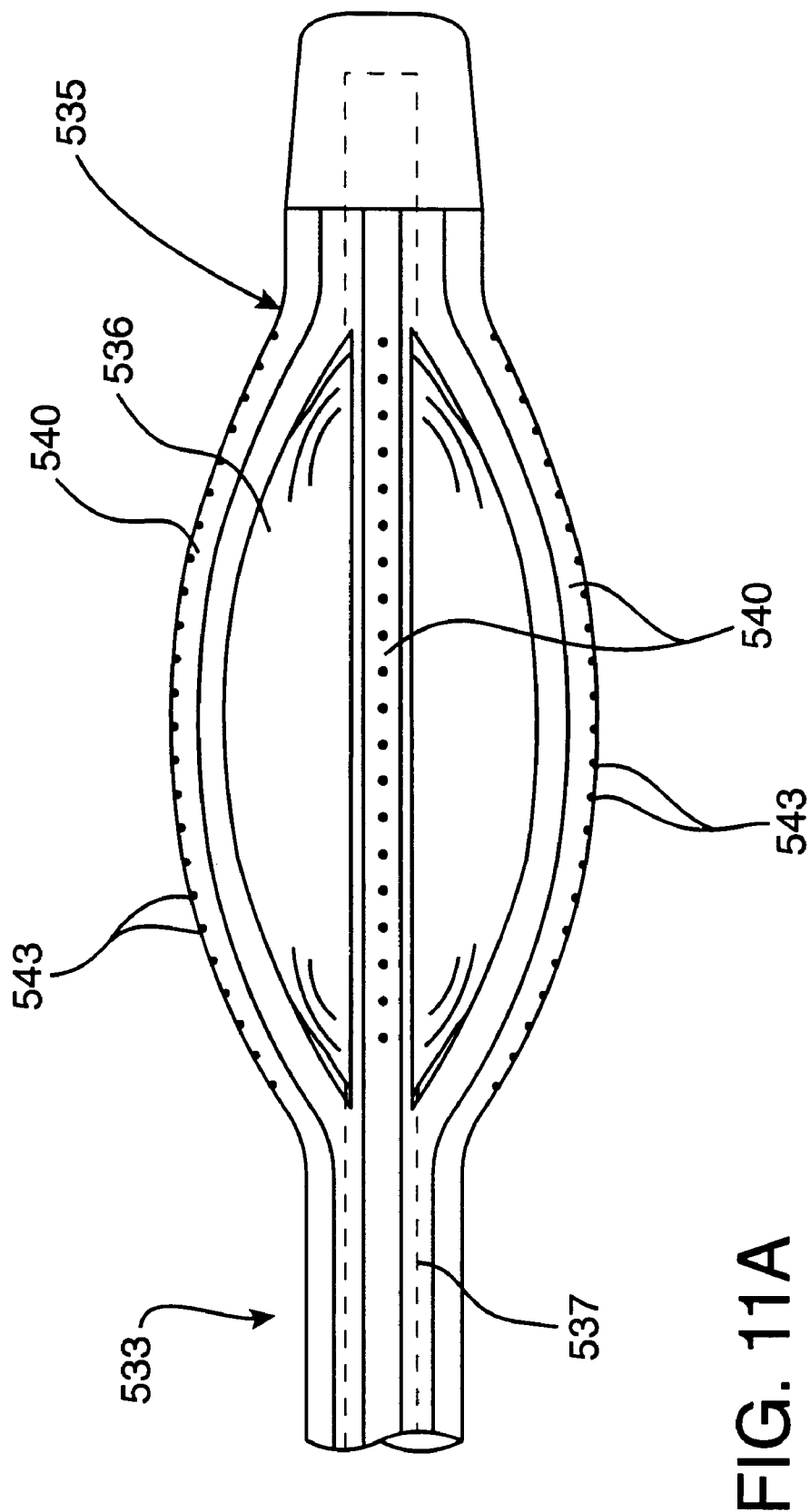

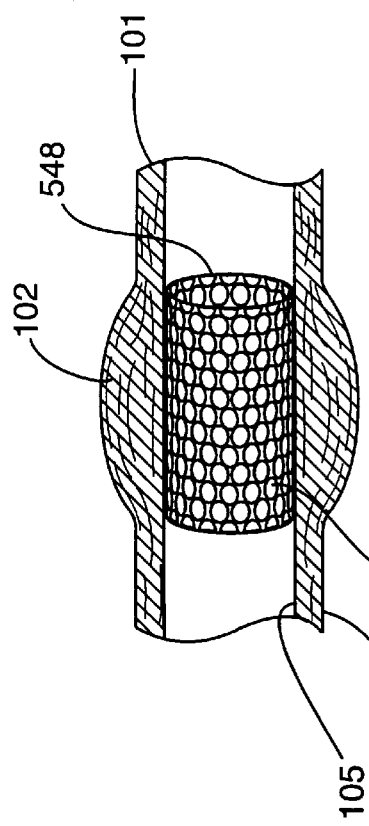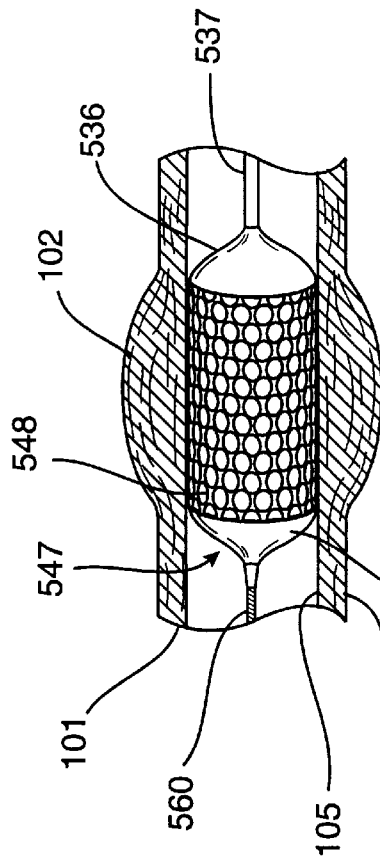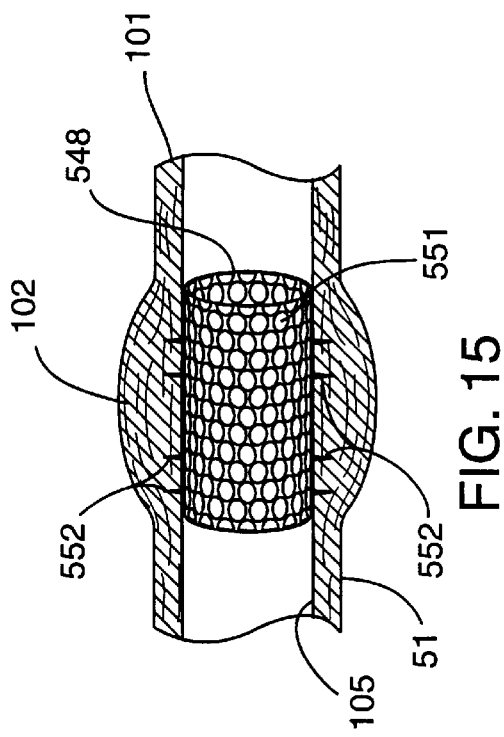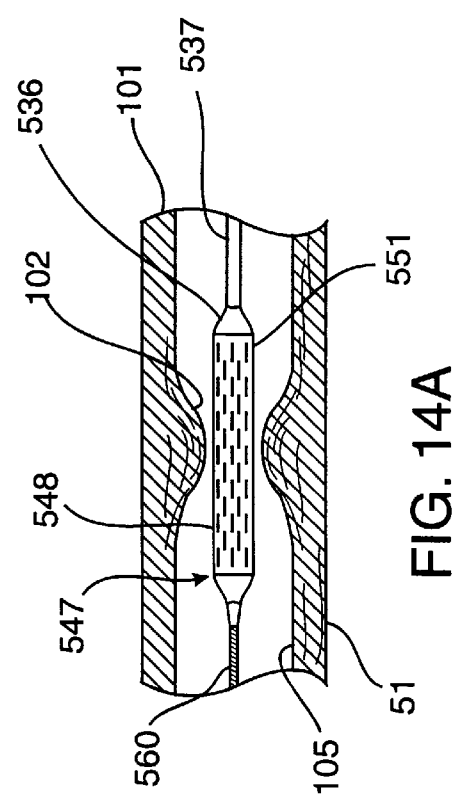

METHOD FOR DELIVERY OF THERAPEUTIC AGENTS TO THE HEART

CROSS-REFERENCE TO RELATED APPLICATIONS

This application is a continuation-in-part of Ser. No. 08/453,426, filed May 30, 1995, now U.S. Pat. No. 5,885,238, which is a divisional application of Ser. No. 08/282,192, filed Jul. 28, 1994, which issued as U.S. Pat. No. 5,584,803. This application is also a continuation-in-part of Ser. No. 08/650,112, filed May 22, 1996, now U.S. Pat. No. 6,029,671, which is a division of Ser. No. 08/415,355, filed Mar. 31, 1995, now abandoned.

BACKGROUND OF THE INVENTION

Recent trends in the advancement of surgical technology have tended toward less invasive procedures in order to reduce trauma to the patient. For example, an important advancement in the area of cardiac surgery is represented by U.S. Pat. No. 5,571,215, and copending patent application Ser. No. 08/281,981, which describe systems for arresting the heart, maintaining circulation of oxygenated blood in the patient and carrying out surgical procedures, such as coronary artery bypass graft (CABG) surgery or heart valve replacement surgery, on the heart.

Another recent therapy is known as Transmyocardial revascularization (TMR) which is a treatment for patients suffering from medically refractory angina pectoris with coronary artery anatomy unsuitable for treatment with more conventional coronary artery bypass grafting or percutaneous transluminal coronary angioplasty. Typically, a high-energy laser is employed to create 20–30 passageways or channels in an ischemic myocardium which penetrate therethrough into the left ventricular chamber. In theory, the channels act as conduits to perfuse oxygenated blood from the left ventricle into the extensive intramyocardial vascular plexus. In essence, at the immediate treated site of the myocardium, the epicardial vasculature is bypassed.

Yet another new technique is molecular enhancement of endothelial cell motility and angiogenesis. One such molecular enhancement is the application of Vascular Endothelial Growth Factors (VEGF) to further stimulate additional angiogenesis. VEGF is a selective mitogen for vascular endothelial cells which has been shown to accelerate endothelial repaving, and attenuate intimal hyperplasia after in vivo arterial injury. D. Weatherford, J. Sackman, T. Reddick, M. Freeman, S. Stevens and M. Goldman, *Vascular endothelial Growth Factor and Heparin in a Biological Glue Promotes Human Aortic Endothelial Cell Proliferation with Aortic Smooth Muscle Cell Inhibition,* SURGERY, August 1996, 433–439. Vascular endothelial growth factor is one of the proangiogenic molecules which include members of the fibroblast growth factor family, transforming growth factor-β, tumor necrosis factor-α, platelet-derived growth factors, as well as other factors. These soluble molecules exert their angiogenic stimuli by coupling to the cell surface receptor and trigger the functions within the endothelial cells through signaling cascades. Engler, D., *Use of Vascular Endothelial Growth Factor for Therapeutic Angiogenesis,* CIRCULATION, 1996;94:1496–1498.

SUMMARY OF THE INVENTION

The present invention provides a system that includes an aortic occlusion device which receives an endovascular device for performing an endovascular procedure on the patient's heart or blood vessels. A bypass system, such as a femoral-femoral CPB system, may be used in conjunction with the aortic occlusion device for maintaining circulation of oxygenated blood in the patient while the heart is arrested. The endovascular procedure can be the only procedure performed on the patient or the procedure can be performed in conjunction with other cardiac surgical procedures such as a CABG or valve procedure.

The aortic occlusion device is preferably introduced percutaneously or by direct cut-down through the femoral artery. This catheter has an occluding member which is able to completely occlude the ascending aorta. The catheter is preferably introduced under fluoroscopic guidance over a suitable guidewire. Transesophageal echocardiography can alternatively be used for positioning the aortic occlusion device.

The aortic occlusion device may serve a number of separate functions and the number of lumina in the catheter will depend upon how many of those functions the aortic occlusion device is to serve. The aortic occlusion device can be used to introduce the cardioplegic agent, normally in solution, into the aortic root via a perfusion lumen. The luminal diameter will preferably be such that a flow of the order of 250–500 ml/min of cardioplegic solution can be introduced into the aortic root to perfuse the heart by way of the coronary arteries. The same lumen can, by applying negative pressure to the lumen from an outside source, effectively vent the left heart of blood or other solutions.

The aortic occlusion device is preferably adapted for introduction of one or more endovascular devices through the lumen of the aortic occlusion device. It is preferable that the diameter and cross-sectional design of the lumens are such that the external diameter of the aortic occlusion device in its entirety is small enough to allow its introduction into the femoral artery by either percutaneous puncture or direct cut-down.

The system also preferably includes a device for delivering a therapeutic agent to the heart. After the occluding member is properly inflated to occlude the ascending aorta, a therapeutic agent delivery device is introduced through the aortic occlusion device. The distal end is guided into one of the main coronary arteries where a therapeutic agent is delivered to the heart through a delivery lumen in the agent delivery catheter. The system can be used to deliver any type of drug or agent to the heart including, but not limited to, proteins, genes, gene vectors, liposome vectors, HJV viral vectors and plasma DNA.

A stent delivery catheter may also be inserted through the lumen of the aortic occlusion device for delivery of a stent. The stent is preferably impregnated with a therapeutic agent so that the stent can deliver the agent to the coronary vasculature.

In another embodiment, the agent delivery device is a needle sheath catheter configured for sliding receipt in the lumen of the aortic occlusion device. An injection catheter is configured for sliding receipt in the needle sheath. A needle is resiliently biased outwardly in a direction sufficiently skewed from a longitudinal axis of the injection catheter to pierce the artery wall upon advancement of the needle. Subsequently, the agent may then be injected through the needle and into the myocardium.

In still another embodiment, the agent delivery device is a therapeutic agent infusion catheter which is advanced through the aortic occlusion device. The infusion catheter includes an expandable infusion array which is expanded to contact the coronary artery wall. The infusion array includes a plurality of laterally-deflectable delivery conduits in communication with a reservoir. The infusion array has a plurality of orifices extending into each one of the conduits for jet infusion of the agent into the coronary artery wall.

The present invention is also directed to a method for delivering an agent to the patient's coronary arteries. The method includes the steps of: placing an aortic occlusion device in a location within a patient's ascending aorta, the aortic occlusion device having an occluding member and a lumen; expanding the occluding member within the patient's ascending aorta to occlude the passageway therethrough; infusing a cardioplegic agent into a coronary vasculature of the patient to arrest the patient's heart; maintaining circulation of the blood downstream of the occluding member; and delivering a therapeutic agent into the coronary vasculature through the aortic occlusion device. The delivering step may be carried out with the aortic occlusion device or with the agent delivery catheter which extends through the aortic occlusion device.

The procedure may also include the steps of occluding the patient's superior and inferior vena cava to isolate the delivery of the therapeutic agent and prevent systemic circulation thereof. Another method of substantially preventing systemic circulation of the agent is to provide a coronary sinus catheter. The coronary sinus catheter is preferably advanced through a peripheral vein, such as the internal jugular vein, with the distal end extending into the patient's coronary sinus. The coronary sinus catheter has an occluding member for occluding the coronary sinus. The coronary sinus catheter has a lumen which withdraws the agent after the agent has passed through the coronary vasculature.

In another aspect of the present invention, the agent may be delivered in a retrograde direction by infusing the agent through the coronary sinus catheter and removing the agent through the lumen in the aortic occlusion device.

In still another aspect of the present invention, the aortic occlusion device is adapted to perform other procedures such as a Transmyocardial Revascularization (TMR) from within the chambers of the heart. TMR is performed by using a side-firing fiberoptic laser catheter introduced through the lumen of the aortic occlusion device and advanced through the aortic valve and into the left ventricle. The side-firing laser catheter is then directed toward the endocardium where a series of channels are cut through the myocardium. In this arrangement, the agent delivered directly to the coronary arteries is preferably vascular endothelial growth factors which stimulate angiogenesis. Although it is preferred to pass the TMR laser through the aortic occlusion device, TMR may be accomplished with a transseptal approach via the intraatrial septum and into the left ventricle.

A number of important advantages accrue from this combination of the aortic occlusion device with these endovascular diagnostic and therapeutic devices and agent delivery capabilities. Introducing a side-firing fiberoptic laser catheter through the aortic occlusion device and subsequent agent delivery allows the patient's heart to be stopped and the circulatory system supported on cardiopulmonary bypass while performing the endovascular procedure and agent delivery. This may allow the application of TMR to patients whose cardiac function is highly compromised and therefore might not otherwise be good candidates for the procedure. It also allows TMR to be performed as an adjunct to other cardiac surgical procedures. With the devices of the prior art, it would be difficult to perform TMR and delivery of an agent since standard aortic cross-clamps prevent devices from being introduced endovascularly. Both TMR and delivery of the agent benefit from performing the procedures while the heart is arrested.

In an alternate mode of operation, the vascular endothelial growth factors may be delivered to the patient's heart by introducing a dispensing instrument into the patient's thoracic cavity. The vascular endothelial growth factors may then be applied to a selected wall of the patient's heart through the dispensing instrument.

To ensure a longer duration of contact between the VEGF and the myocardium to further stimulate angiogenesis, the vascular endothelial growth factors may be suspended in a viscous liquid, such as a fibrin based glue or a bioabsorbable polymer gel. These viscous liquids have a greater likelihood of extended exposure to the treated regions where a longer exposure duration to VEGF may be advantageous.

Additionally, timed release delivery of the VEGF to the heart can be accomplished with a patch which is placed into direct contact with the myocardium. The patch would contain the therapeutic agent which would be continuously delivered to the myocardium over an extended period of time. The agent delivery material may be provided by various structures including a suture composed of an absorbable polymer wherein the growth factors are encapsulated therein. In another embodiment, the agent delivery material may be provided by a relatively flat absorbent patch device sutured to the epicardium of the heart.

These and other aspects of the present invention will become apparent from the following description of the preferred embodiments, drawings and claims.

BRIEF DESCRIPTION OF THE DRAWINGS

FIGS. 10A and 10B are a sequence of fragmentary, enlarged side elevation views, in cross-section, of a needle tip portion of the needle injection catheter of FIG. 9 being advanced past a needle sheath and penetrating the coronary artery wall for delivery of a therapeutic agent.

FIG. 11A is a fragmentary, enlarged side elevation view of an inflated jet infusion catheter.

FIGS. 14A and 14C are a series of fragmentary, enlarged side elevation views, in cross-section, of the stent delivery catheter of FIG. 13 implanting the stent across the stenosis.

FIG. 15 is a fragmentary, enlarged side elevation view, in cross-section, of an alternative embodiment of the stent of FIG. 13 having delivery needles.

DETAILED DESCRIPTION OF THE INVENTION

Figure 1:
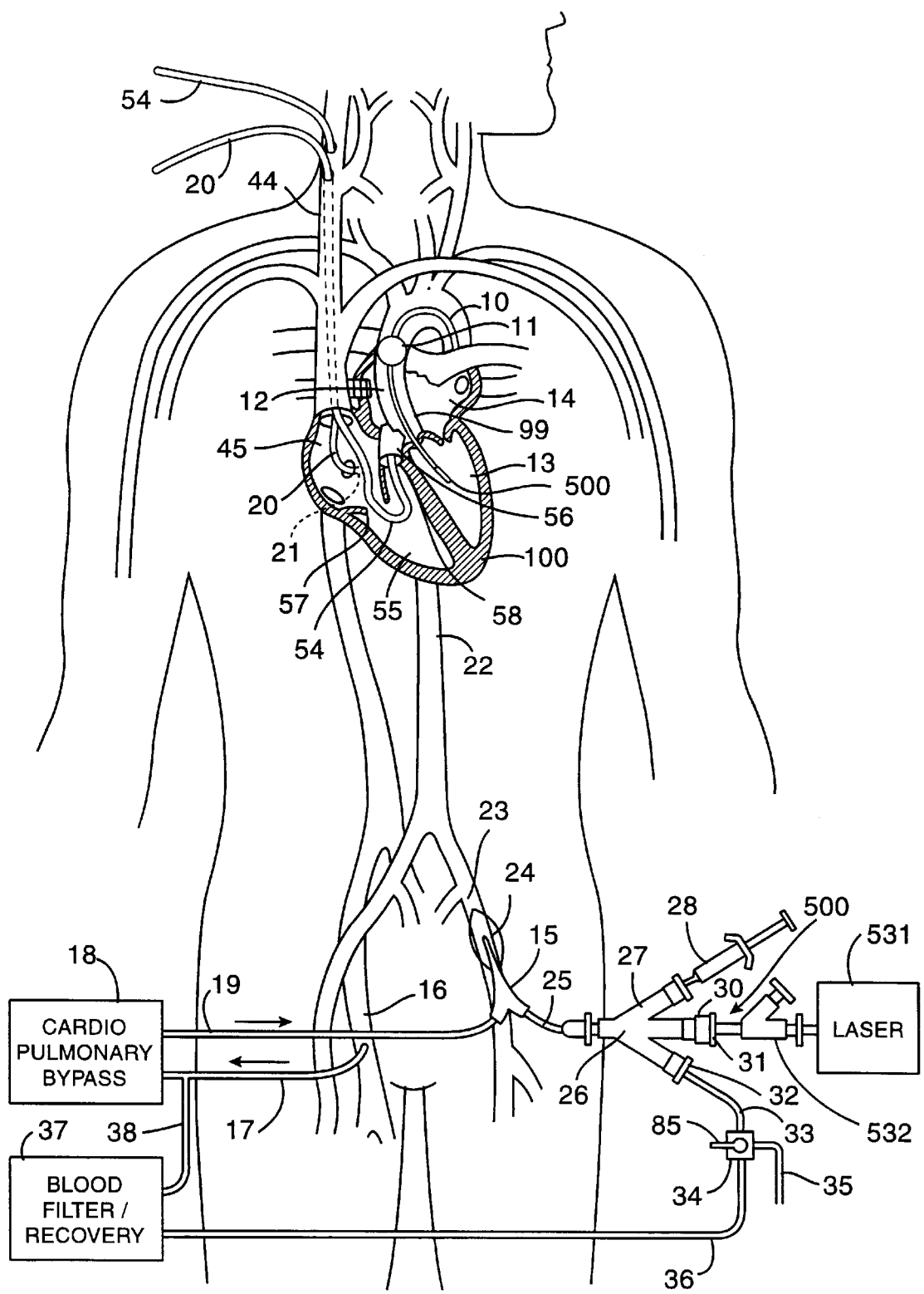
FIG. 1 schematically illustrates a system for performing endovascular procedures embodying features of the invention.

Referring to FIG. 1, a schematic depiction of a system in accordance with the present invention is shown. The system includes an aortic occlusion device 10 and a coronary sinus catheter 20. The aortic occlusion device 10 has an occluding member 11 for occluding the ascending aorta 12 and the coronary sinus catheter 20 has an occluding member 554 for occluding the coronary sinus 21. The aortic occlusion device 10 is advanced through an arterial cannula 15 which is positioned in femoral artery 23. A bypass system 18 removes blood from the femoral vein 16 through venous cannula 17, oxygenates the blood, and returns the oxygenated blood to the patient through the arterial cannula 15. Cardioplegic fluid is delivered through one or both of the aortic occlusion device 10 and the coronary sinus catheter 20 to paralyze the myocardium.

The proximal end 25 of the aortic occlusion device 10 has an adapter 26 with an inflation lumen 27 coupled to an inflation device 28 for inflating the occluding member 11. A main lumen 30 splits into a first arm 30 having a hemostasis valve 31 through which an endovascular device may be inserted into the main lumen 30. The main lumen 30 is also coupled to a source of cardioplegic fluid (not shown) which is delivered through the main lumen 30 to arrest the patient's heart. A second arm 32, which also leads to the main lumen 30, is coupled to a blood filter/recovery unit 37 for venting blood from the ascending aorta through the main lumen 30.

Figure 2:
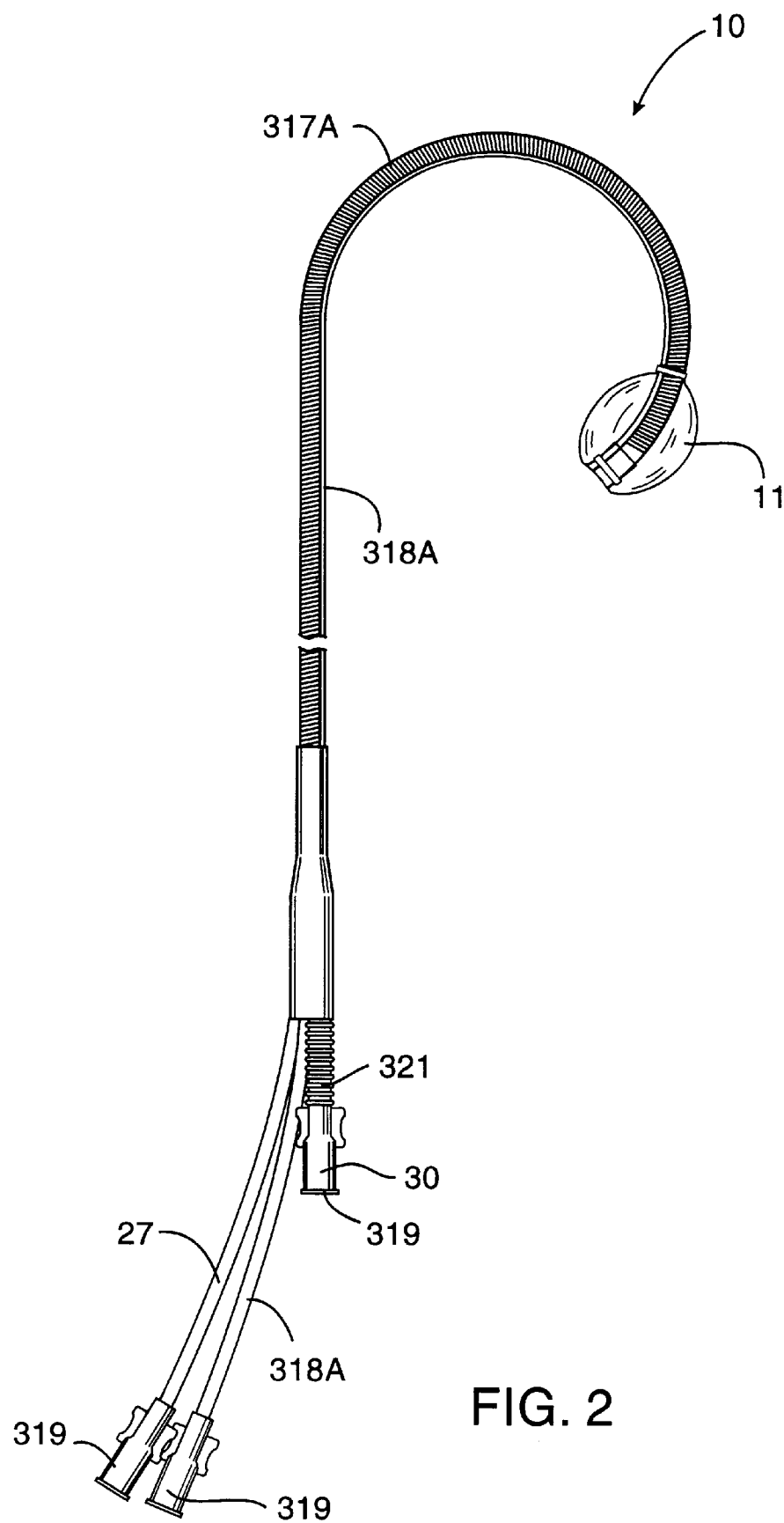
FIG. 2 is a side view of an aortic occlusion device.
Figure 3:
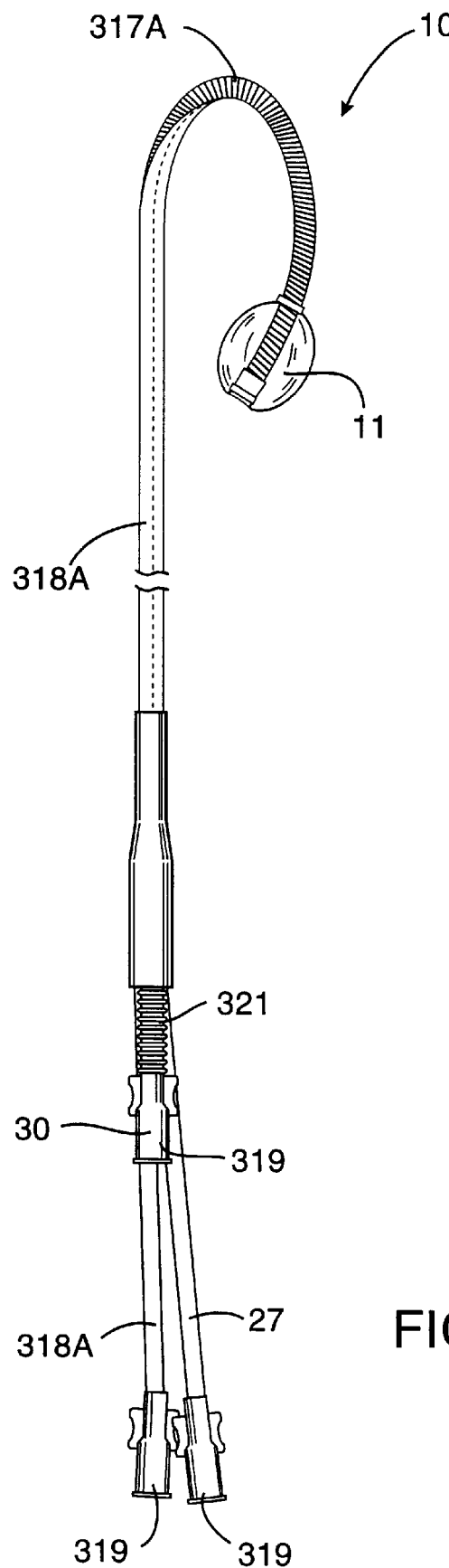
FIG. 3 is another side view of the aortic occlusion device of FIG. 2.

Referring to FIG. 2, a more detailed view of the aortic occlusion device 10 is provided which shows the main lumen 30, inflation lumen 27 and a pressure lumen 318A for measuring pressure in the ascending aorta. Each lumen 30, 27, 318A has a connector 319 at a proximal end and the main lumen 30 has a bellows 321 connection to increase flexibility and prevent kinking. The connector 319 is attached to the hemostasis valve 31 (see FIG. 1) and the second arm 32 (see FIG. 1) so that the main lumen 30 can be used to deliver cardioplegic fluid, vent the ascending aorta and receive an endovascular device. A curved distal portion 317A facilitates positioning the occluding member 11 in the ascending aorta. Referring to FIG. 3, the curved distal portion 317A is also preferably offset somewhat. The resulting curved distal portion 317A generally conforms to the aortic arch to facilitate placement of the occluding member 11 in the ascending aorta.

Figures 5A, 5B:
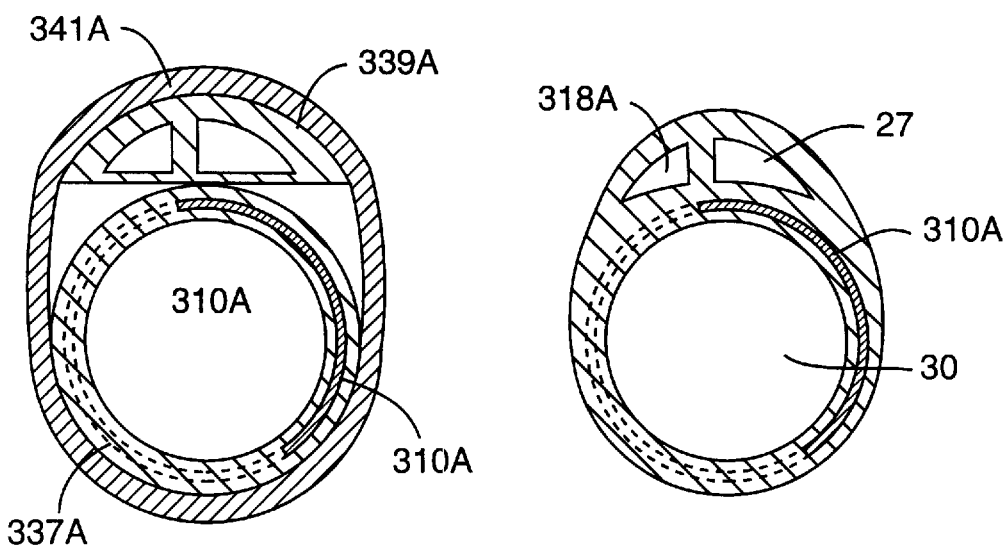
FIG. 5A is a cross-sectional view showing the manufacture of the aortic occlusion device of FIG. 2.
FIG. 5B is a cross-sectional view of the structure of FIG. 5A after heating.

Referring to FIG. 5B, a cross-section of the aortic occlusion device 10 is shown. The cross-sectional shape of the aortic occlusion device 10 is somewhat egg-shaped but may, of course, also be substantially circular or any other suitable shape. An elongate element 310A, which is described below, reinforces the aortic occlusion device 10.

Figure 4A:
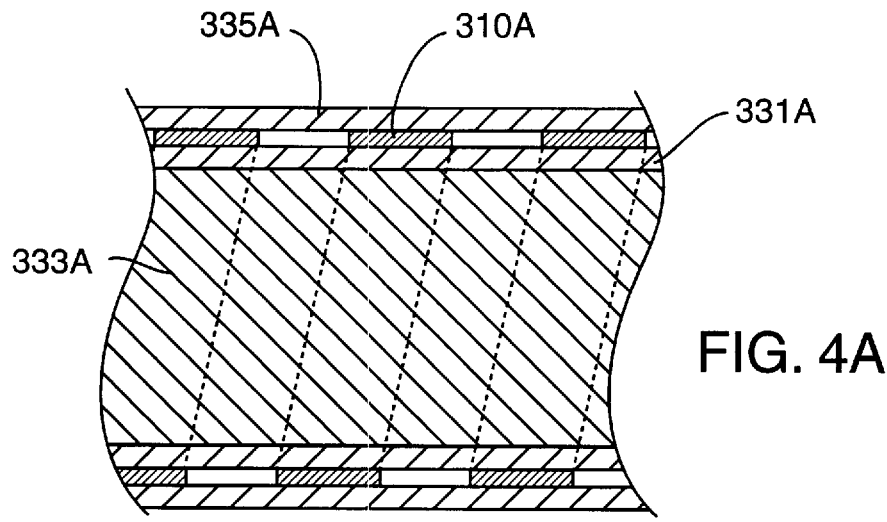
FIG. 4A is a longitudinal cross-sectional view showing the method of constructing the device of FIG. 2.
Figure 4B:
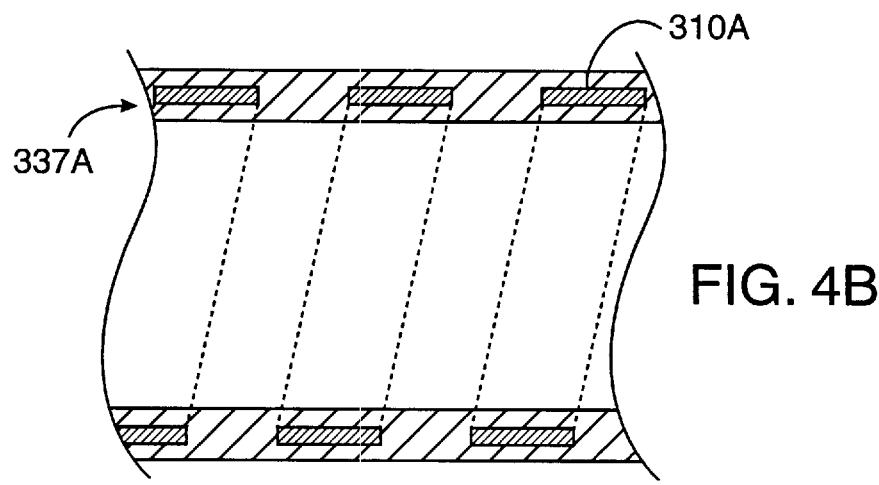
FIG. 4B is a longitudinal cross-sectional view showing the structure of FIG. 4A after heating.

Referring to FIGS. 4A, 4B, and 5A, a preferred method of forming the aortic occlusion device 10 is shown. FIG. 4A shows a longitudinal cross-section of a tube 331A, preferably a urethane tube, mounted on a mandrel 333A with the reinforcing elongate element 310A wound around the tube 331A in a helical manner. The elongate element 310A is preferably a wire ribbon having a thickness of 0.003 inch and a width of 0.012 inch. The elongate element 310A is preferably wrapped around the tube 331A with a spacing of 0.010 inch. Another tube 335A is positioned over the elongate member 310A and a shrink tube (not shown) is positioned over the tube 335A. The entire structure is then heated to fuse the tubes together to form a reinforced tube 337A which is shown in longitudinal cross-section in FIG. 4B. The resulting reinforced tube 337A preferably has an inner diameter of about 0.100 inch and a wall thickness of about 0.010 inch.

Referring to FIG. 5A, a two-lumen member 339A is positioned against the reinforced tube 337A and a shrink tube 341A is positioned around the member 339A and reinforced tube 337A. The two-lumen member 339A has the inflation lumen 320A and the pressure lumen. The two-lumen member 339A is preferably an extrusion having a D-shaped outer surface in cross-section. The member 339A and tube 337A are then heated and the shrink tube 341A is removed to obtain the egg-shaped cross-sectional shape shown in FIG. 5B. The cross-sectional shape is preferably about 0.145 inch tall and 0.125 inch wide. The inflation lumen 320A is then pierced to provide an inflation path to the occluding member 315 and the occluding member 315 is then mounted to the aortic occlusion device 10.

Although it is preferred to use the aortic occlusion device 10 described above, other aortic occlusion devices may be used such as the devices of U.S. Pat. No. 5,478,309 to Sweezer, U.S. Pat. No. 5,433,700 to Peters, and U.S. Pat. No. 5,556,412 to Hill which are hereby incorporated by reference. The arterial cannula may be any conventional arterial cannula and is preferably the arterial cannula described in co-pending Ser. No. 08/749,683, filed Nov. 15, 1996 by David Snow, which is also hereby incorporated by reference. Furthermore, the arterial cannula 15 and/or aortic occlusion device 10 may be introduced through an artery superior of the aortic arch, such as the subclavian artery, as taught by U.S. Pat. No. 5,584,803 to Stevens or directly into the aortic arch as taught by U.S. Pat. No. 5,556,412 to Hill. Although it is preferred to be able to separate the aortic occlusion device 10 from the arterial cannula 15, the functions of the aortic occlusion device 10 and the arterial cannula 15 may be combined into a single, multi-channel catheter as shown in U.S. Pat. No. 5,433,700 to Peters.

Figure 16:
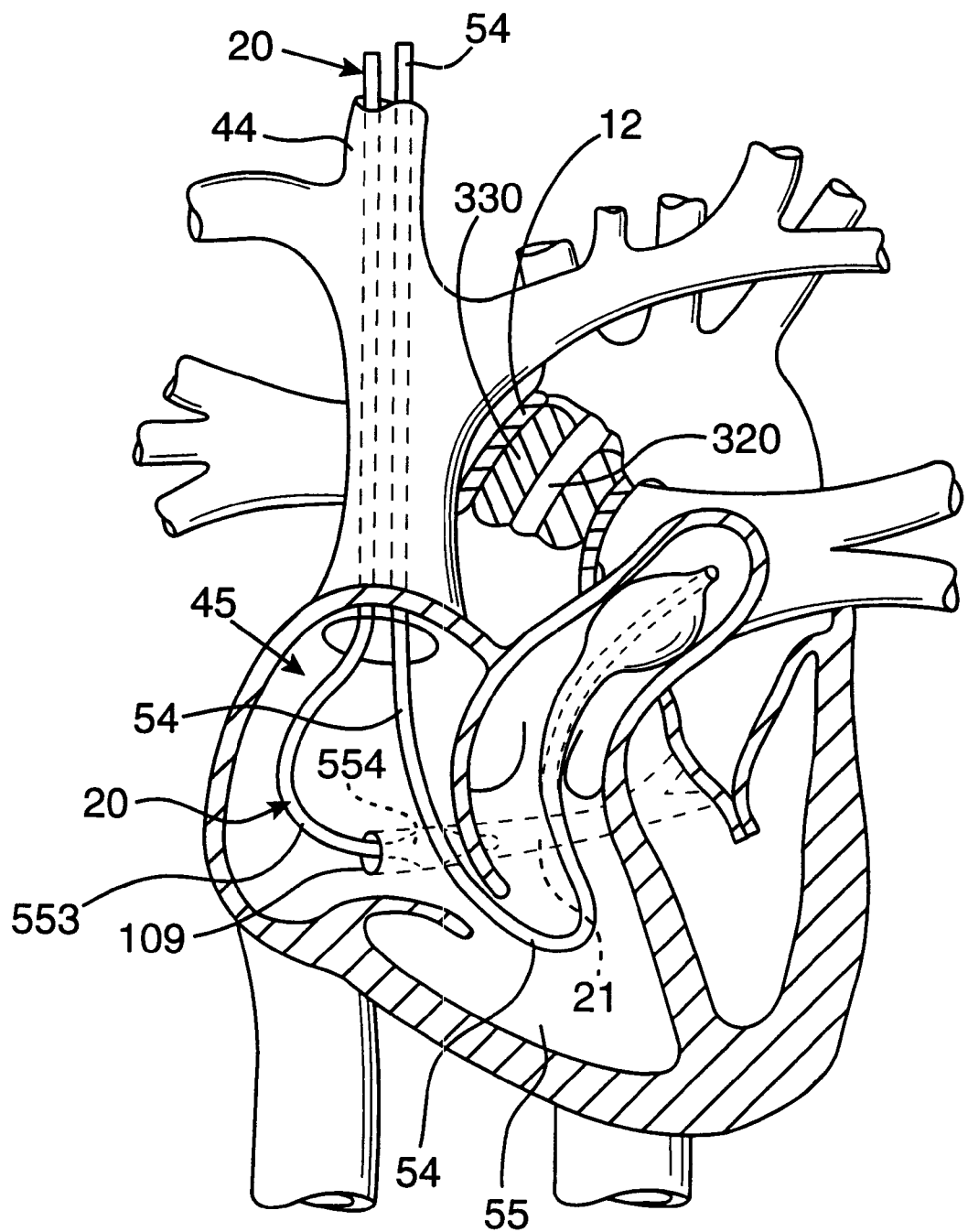
FIG. 16 is an enlarged, fragmentary, top perspective view, in partial cross-section, of a patient's heart with an aortic occlusion device placed in the ascending aorta adapted to deliver a therapeutic agent to the coronary vasculature of the heart, in combination with a coronary sinus catheter and a pulmonary venting catheter to isolate the delivered therapeutic agent from systemic circulation.

Referring again to FIGS. 1 and 16, the coronary sinus catheter 20 is introduced into the patient's venous system through the right internal jugular vein 44 and is advanced through the right atrium 45 and into the coronary sinus 21. The coronary sinus catheter 20 is provided with a flexible shaft 553 having a occlusion balloon 554 for occluding the coronary sinus 21. A vent catheter 54 (FIG. 1) is advanced through the internal jugular vein 44 and extends through the right atrium 45 and right ventricle 55 into the pulmonary trunk 56. The vent catheter 54 passes through tricuspid valve 57 and pulmonary valve 58 for venting blood from the pulmonary artery.

Figure 6:
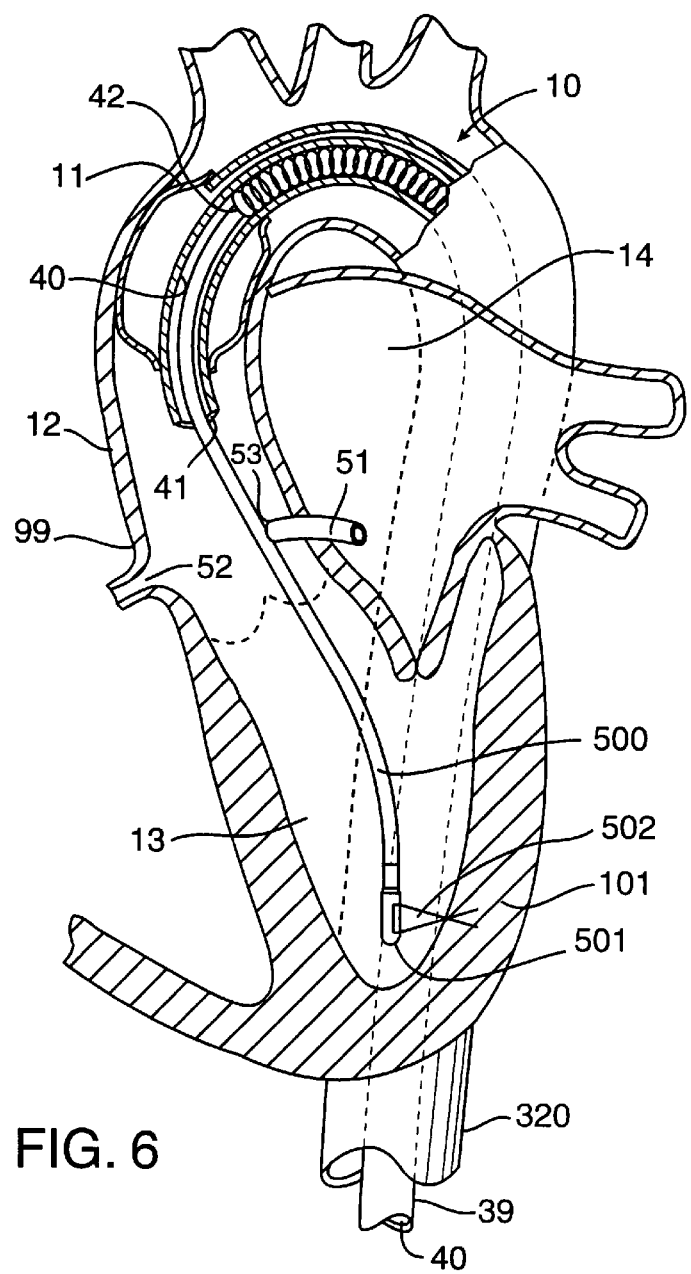
FIG. 6 is a view of a patient's heart with the aortic occlusion device placed in the ascending aorta and with a side-firing fiberoptic laser catheter performing transmyocardial revascularization from within the left ventricle of the heart.
Figure 9:
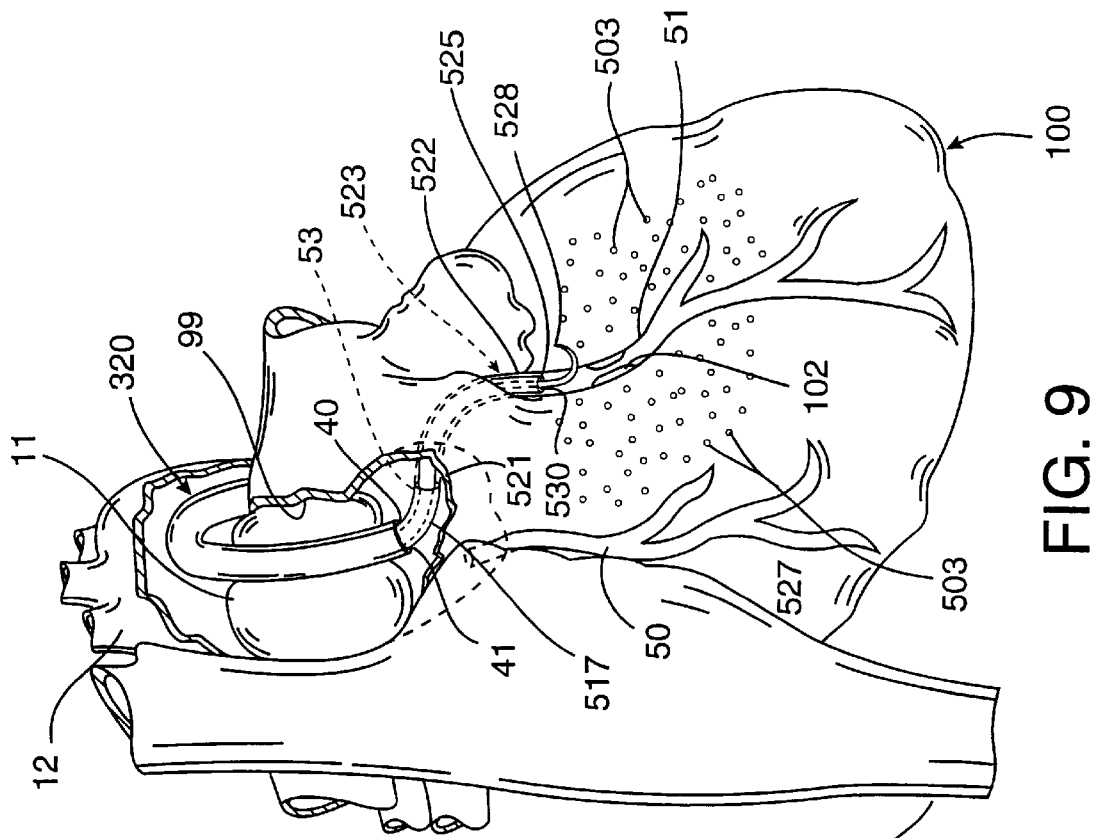
FIG. 9 is a fragmentary, top perspective view of a patient's heart with the endoarotic partitioning device placed in the ascending aorta and illustrating an needle injection catheter advanced through a lumen in the partitioning catheter and penetrating a coronary artery wall for delivery of a therapeutic agent.
Figure 8:
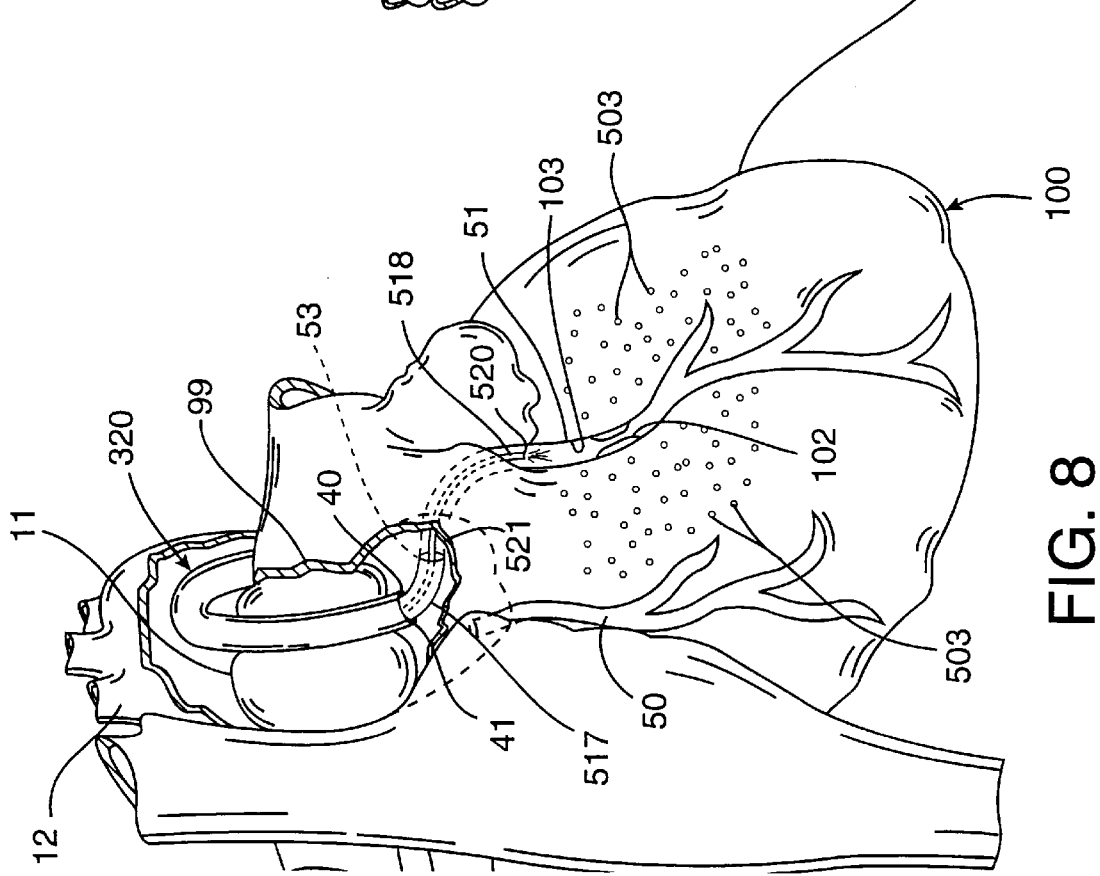
FIG. 8 is a fragmentary, top perspective view of a patient's heart with the endoarotic partitioning device placed in the ascending aorta and illustrating a therapeutic agent delivery catheter advanced through a lumen in the partitioning catheter and placed within a coronary artery for delivery of a therapeutic agent.

Referring to FIG. 6, a schematic representation of a patient's heart 100 partly cut-away is shown. The occluding member 11 is inflated to occlude the ascending aorta to separate the coronary arteries from the remainder of the circulatory system. An endovascular device for performing a diagnostic or therapeutic procedure, represented here by a side-firing fiberoptic laser catheter 500 coupled to a laser device 531, is introduced into the patient through the main lumen 40 of the aortic occlusion device 10. In this illustrative example, a side-firing fiberoptic laser catheter 500 has been introduced through the aortic occlusion device 320 for performing TMR. The proximal end of laser catheter 500 is coupled to laser device 531. The distal tip 501 of the catheter 500 is positioned to direct a focused beam of laser energy 502 at the wall 101 of the left ventricle 13 to open a blood flow passage into the myocardium. In an alternate mode of operation, the side-firing fiberoptic laser catheter 500 can be introduced into one or more of the patient's coronary arteries and the laser beam 502 directed toward the left ventricle 13 to open a blood flow passage from the ventricle 13 into the coronary artery. This technique is repeated until about twenty to thirty (20–30) one millimeter diameter holes 503 are formed in the ventricle as shown in FIGS. 8 and 9.

Figure 7:
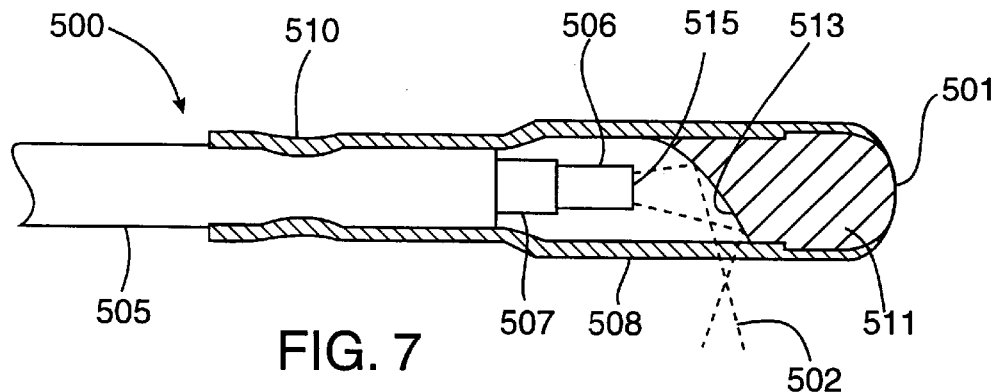
FIG. 7 is a cross section of tip of the side-firing fiberoptic laser catheter.

Referring to FIG. 7, the side-firing fiberoptic laser catheter 500 has a shaft 505 containing an optical fiber 506 surrounded by cladding 507. A housing 508, which is preferably made of stainless steel, is attached to the shaft 505 with a crimp 510. A reflective insert 511 is positioned within the housing 512. The insert 511 has a highly reflective surface 513 which deflects the laser through an aperture 516 in the side of the housing 512. A highly polished gold surface, provided by making the reflective insert 511 of gold or by plating a gold coating onto the reflective surface 511, can reflect up to 98% of the incident laser energy. The reflective surface 511 can be polished in a curve as shown so that the laser beam is focused at a selected distance from the catheter distal tip 501 to control the depth to which the blood flow passages are opened into the myocardium. Specific examples of other suitable laser catheters 500 are described in the following patents which are hereby incorporated by reference: U.S. Pat. Nos. 5,354,294, 5,366,456, 5,163,935, 4,740,047, 5,242,438, 5,147,353, 5,242,437, 5,188,634, 5,026,366, and 4,788,975.

The combination of the laser catheter 500 with the aortic occlusion device 10 allows the patient's heart to be stopped and the circulatory system supported on cardiopulmonary bypass during the procedure. This allows for more precise placement of the myocardial channels. It also allows the combination of TMR with other cardiac procedures that may be performed on the patient while the heart is stopped. The same holds true if the laser catheter 500 is used for ablation of other material within the heart or the blood vessels including ablation of an electrophysiological node within the heart walls for treatment of atrial or ventricular tachycardia or other electrophysiological problems.

After completion of the first endovascular procedure, another endovascular procedure may commence. In particular, once TMR has been performed an agent may be delivered to heart. Referring to FIG. 8, a coronary guiding catheter 517 is introduced through the lumen 40 of the aortic occlusion device 320. After the coronary guiding catheter is properly positioned in a coronary ostia, an agent delivery catheter 518 is advanced through lumen 521 of the coronary guiding catheter 517 and into the coronary artery 51. The agent delivery catheter provides a delivery port 520 proximate a distal end thereof for delivery of the agent. In most instances, as shown in FIGS. 8 and 9, the delivery port 520 of the agent delivery catheter 518 is to be positioned just upstream from the stenosis 102 for delivery of the agent. The agent may be any suitable agent includes vascular endothelial growth factor (VEGF).

Figure 11B:
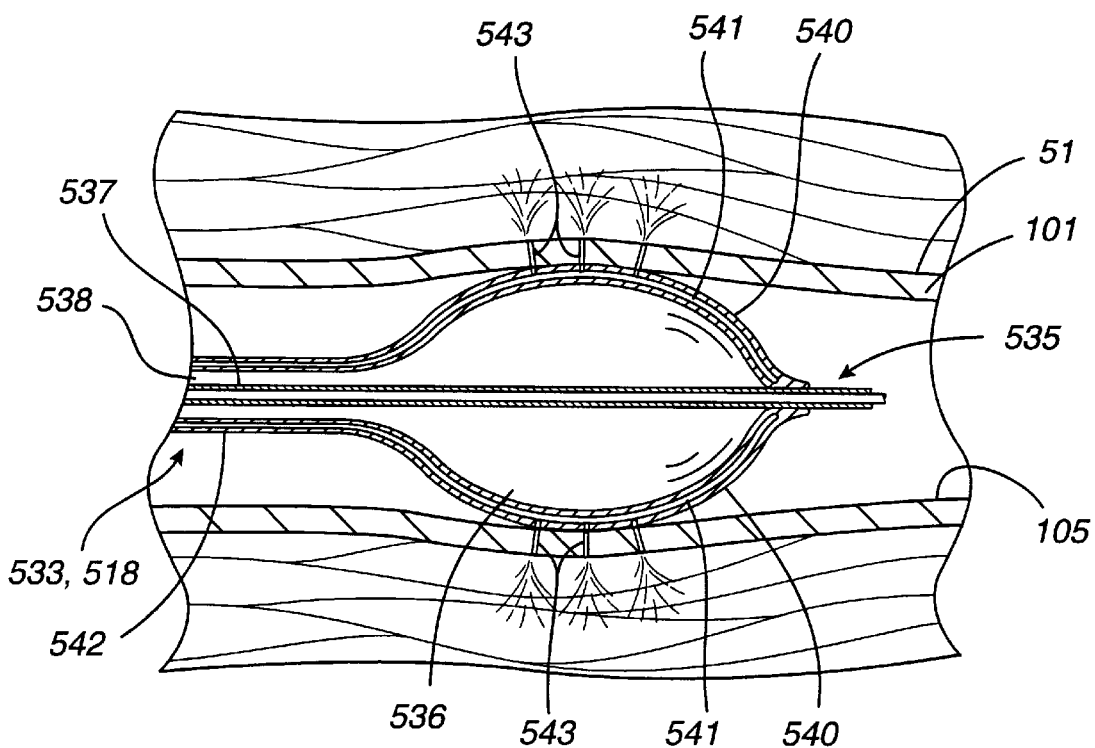
FIG. 11B is a fragmentary, enlarged side elevation view, in cross-section, of an inflated jet infusion catheter infusing agent into the coronary artery.
Figure 13:
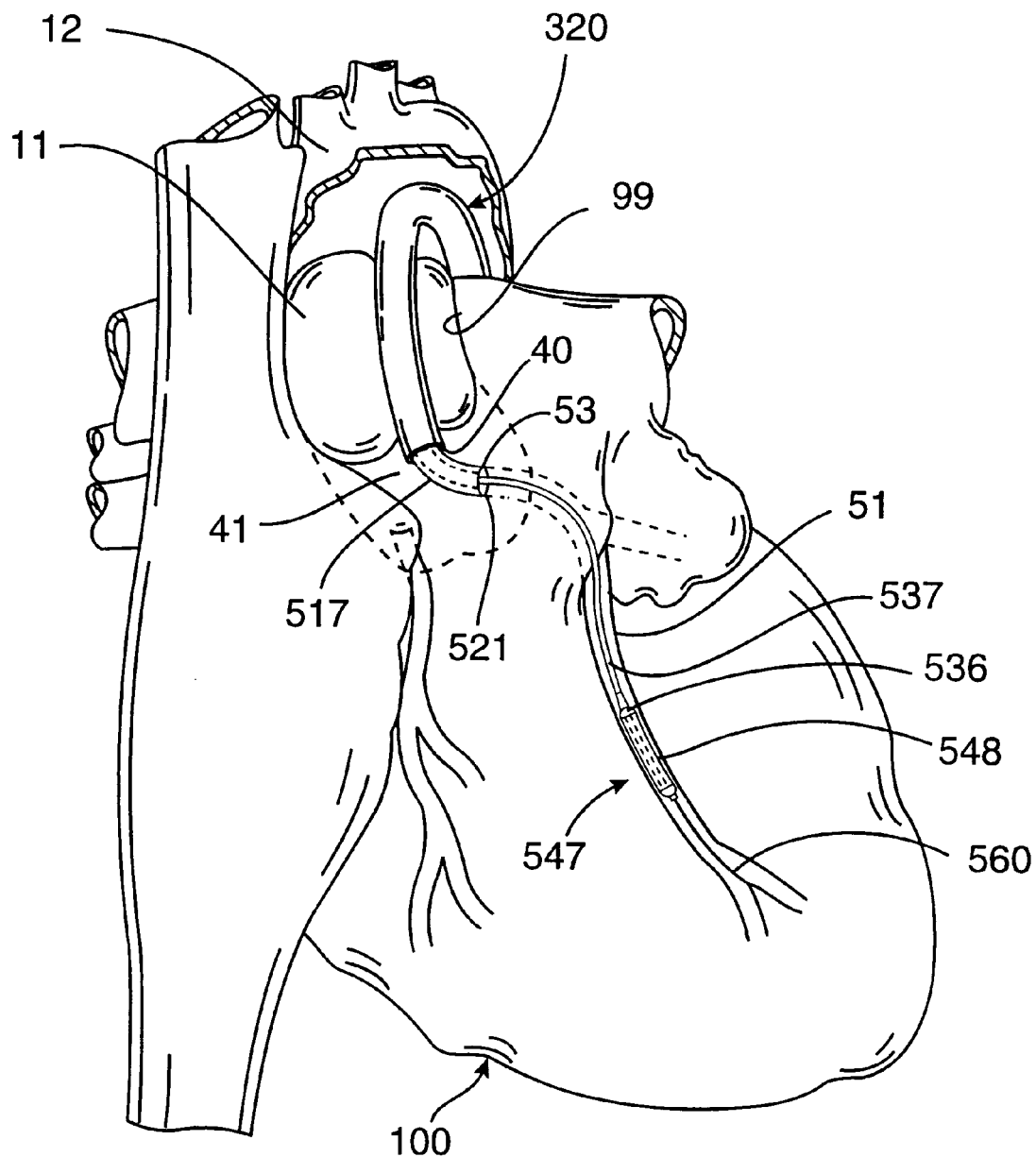
FIG. 13 is a fragmentary, top perspective view of a patient's heart with the aortic occlusion device placed in the ascending aorta and illustrating stent delivery catheter placed within a coronary artery for placement of a stent impregnated with a therapeutic agent for timed release delivery of the agent to the myocardium.

Another agent delivery technique is to inject the agent directly into the myocardium by piercing the artery wall 103 of the coronary artery. Such delivery may be accomplished through either needle injection (FIGS. 9 and 10B) or jet infusion (FIG. 11A and 11B). For needle injection a needle sheath 522 (FIGS. 10A and 10B) is advanced and guided into one of the coronary ostia 53 using the guiding catheter 517. The sheath is advanced through the coronary artery to a position upstream from the desired region of delivery. Once the needle sheath 522 is properly positioned, a needle catheter 523 is advanced through the needle sheath 522. A needle 527 having a delivery tip 528 is configured to pierce the coronary artery wall 103. As best illustrated in FIG. 10B, the needle 527 is preferably hooked or C-shaped and is biased outwardly relative to a longitudinal axis of the flexible shaft 526 of the injection catheter 523. It will be understood that needle 527 is flexible to enable advancement of the injection catheter 523 through the needle sheath 522. Needle 527 is preferably made a material sufficiently rigid to enable piercing of the artery wall yet sufficiently flexible enough so that the needle 527 can be straightened for advancement through the needle sheath 522. Suitable materials for the needle 527 include stainless steel and NiTi or other shape memory alloys. It will be understood that needle 527 may include two or more tips each biased outwardly. Further, the needles can be biased outwardly using angled passages extending through the walls of the catheter (not shown). A syringe is attached to a fitting 532 (FIG. 1) to supply agent to the needle 527.

An alternative technique for delivery of the agent is jet infusion. Referring to FIG. 11A, an infusion catheter 533 has an array 535 formed to infuse agent through the coronary artery wall and into the myocardium. The catheter 533 has a balloon 536 mounted to a shaft 537 with the array 535 positioned around the balloon 536. A syringe or other inflation device (not shown) is coupled to an inflation lumen 538 for inflating the balloon 536.

In a preferred form, the array 535 includes a plurality of spaced-apart deflection members 540 extending around the balloon which are formed to deflect toward the intimal surface of the coronary artery 51 during inflation of the balloon. Each deflection member 540 includes a conduit 541 which is in fluid communication with an agent lumen 542. In turn, the agent lumen 542 is coupled to an injection mechanism (not shown) for infusion of the agent. A plurality of orifices 543 (about 10–50 $\mu$m) extend from the deflection members for jet infusion delivery of the agent.

After proper positioning of the catheter 533 in the coronary artery, the balloon 536 is inflated to expand the infusate array 535 into contact with the coronary artery wall. The agent is then delivered through the orifices 543 so that the agent penetrates the coronary artery wall and is infused into the myocardium. After delivery of the agent, which may be VEGF after a TMR procedure, the balloon 536 is deflated so that the catheter 518 can be withdrawn. Examples of infusion array catheters 533 and other intravascular agent delivery catheters are described in the following patents which are hereby incorporated by reference: U.S. Pat. Nos.: 5,419, 777; 5,354,279; 5,336,178; and 5,279,565.

Figure 12:
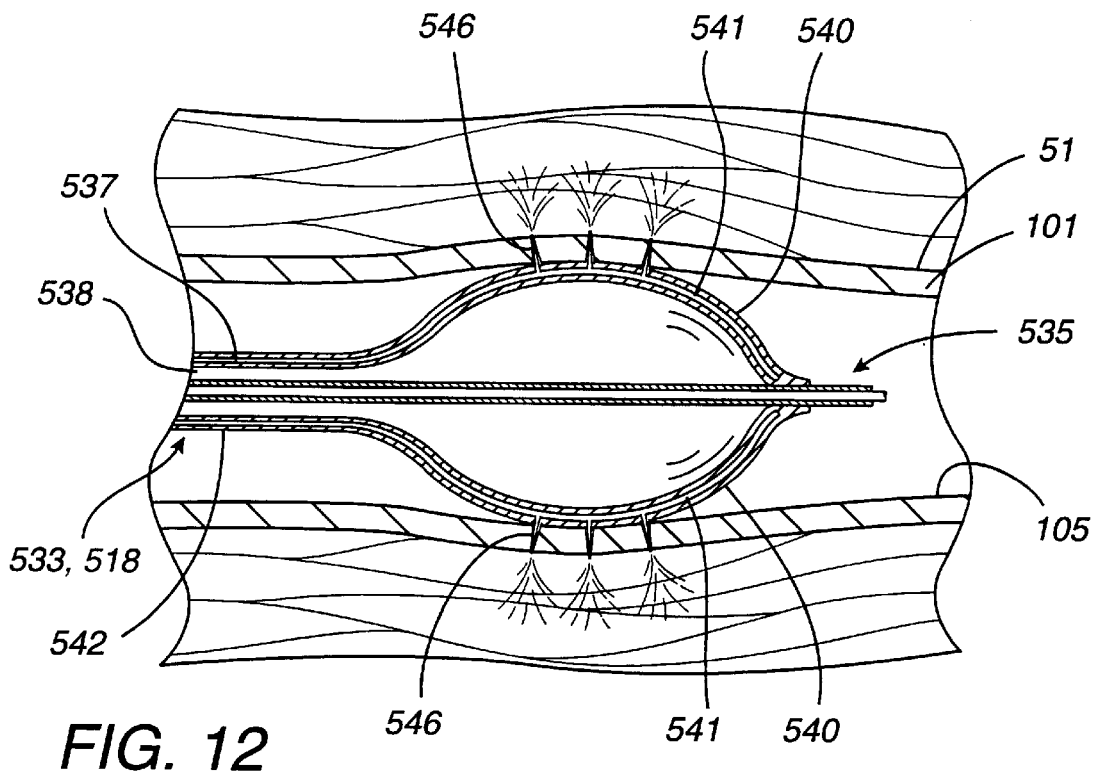
FIG. 12 is a fragmentary, enlarged side elevation view, in cross-section, of an alternative embodiment of the inflated jet infusion catheter of FIG. 11 having injection needles.

In an alternative embodiment, as shown in FIG. 12, each deflection member 540 of the infusion array 535 may include a plurality of injection needles 546 positioned radially outwardly therefrom. Each needle 546 is coupled to the corresponding conduit and each is formed to pierce through the coronary artery wall when the balloon is inflated to deliver agent into the myocardium.

Turning now to FIGS. 13 and 14A–14C, another agent delivery system is illustrated combining a stent delivery catheter 547 with the aortic occlusion device 320. In this configuration, a stent 548 is delivered and implanted in the coronary artery. The stent is preferably impregnated with the desired agent for timed release to the surrounding vascular plexus. The stent delivery catheter 547 is advanced through a guiding catheter 517 which is advanced through the aortic occlusion device 320 in the manner described above.

The stent delivery catheter 547 has a balloon 536 mounted to a shaft 537. The stent 548 is mounted, in a compressed state, over the balloon 536. A fluid-filled syringe or other inflation device (not shown) is used to inflate the balloon 536. A guidewire 560 may be used to advance the stent delivery catheter 547 through the coronary artery 51 to the site of a coronary stenosis 102. The balloon 536, which is deflated with the stent 548 mounted thereon, is then advanced across the stenosis 102 as shown in FIG. 14A. FIG. 14B illustrates that when the balloon 536 is inflated, the stent 548 is expanded to dilate the stenosis 102. The balloon 536 is then deflated and the catheter 547 is withdrawn leaving the stent 548 in the coronary artery 51 (FIG. 14C).

The stent 548 is preferably impregnated with a therapeutic agent for delivery to the myocardium in a timed release manner. The stent is preferably composed of a conventional stent material such as stainless steel, NiTi or other shape memory alloys. A bioabsorbable coating 551, impregnated with the desired agent, is coated over stent 548 so that the agent can be absorbed into the myocardium through the coronary artery wall. Accordingly, once the stent 548 is properly positioned and expanded in the coronary artery 51 to dilate the stenosis 102 (FIG. 14C), the timed release of the agent directly to the vasculature of the myocardium can commence. Suitable bioabsorbable coatings may include fibrin based glues, absorbable polymers, and ethylene vinyl acetate copolymers, waxes, hydrophilic gums, hydrogels, poly(othoesters), poly(orthocarbonates). Other bioabsorbable coatings suitable for use with the present invention are disclosed in U.S. Pat. No. 5,518,730, hereby incorporated by reference. Alternatively, stent 548 itself may be composed of a bioabsorbable material which is impregnated with a therapeutic agent. Examples of balloons suitable for expanding a coronary artery stent are described in U.S. Pat. Nos. 5,055, 024 and 4,490,421 which are hereby incorporated by reference,. Examples of arterial stents and stent delivery catheters are described in U.S. Pat. Nos. 5,041,126, 4,856, 516 and 5,037,392 which are hereby incorporated by reference.

Referring to FIG. 15, the stent 548 has needles 552 protruding radially outward to penetrate the coronary artery wall 103. Upon inflation of the balloon 536, the needles 552 are urged through the intimal surface 105 of the coronary artery wall. The needles 552 not only provide anchor the stent 548 but also provide a conduit for delivery of the agent into the surrounding myocardium.

The agent may also be simply through the main lumen of the aortic occlusion device 10 or the coronary sinus catheter 20. Delivery of the agent, such as VEGF, may be independent or simultaneous with the delivery of cardioplegic fluid. When the agent is VEGF, it is preferable to deliver the agent at the end portion of the delivery cycle of the cardioplegic agent. Preferably, this delivery occurs during at least about the last one-third of the total duration of one full cycle of the infusing step. After delivery of the agent, the infusion is stopped for a predetermined time to enable absorption of the VEGF or therapeutic agent into the vasculature of the heart.

Since the agent delivered may be potent, such as VEGF, systemic circulation may be undesirable. Thus, after delivery of the agent, containment or isolation of the therapeutic agent is desirable. One particular advantage of the present invention is that the eventual dispersion of the VEGF to the systemic circulation can be minimized. The aortic occlusion device 10, coronary sinus catheter 20 and vent catheter 54 cooperate to remove the agent so that the agent is not released into the systemic circulation. When the agent is delivered antegrade through the aortic occlusion device 10, the coronary sinus catheter 20 withdraws the agent. When the agent is delivered retrograde through the coronary sinus catheter 20, the agent is withdrawn through the aortic occlusion device 320. The vent catheter 54 can be used to remove fluids and agents from the pulmonary artery whether the fluids or agents are delivered through the aortic occlusion device 10 or the coronary sinus catheter 20.

Figure 17:
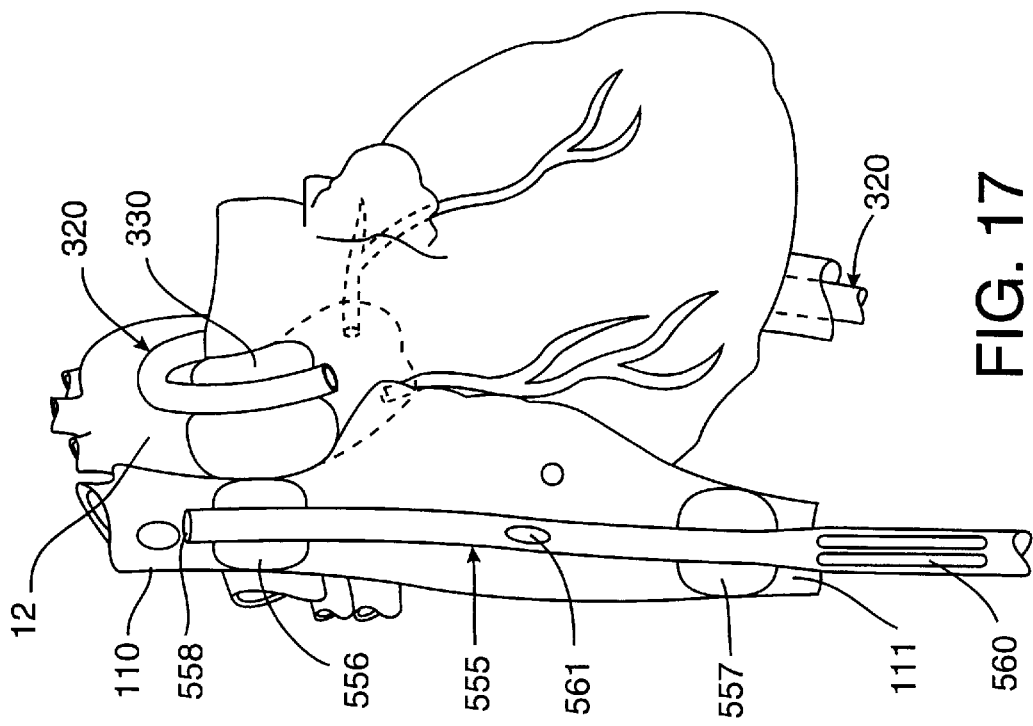
FIG. 17 is an enlarged, fragmentary, top perspective view, in partial cross-section, of a patient's heart with an aortic occlusion device placed in the ascending aorta, and a single venous double-balloon catheter which collectively isolate the delivered therapeutic agent from systemic circulation.

Systemic isolation and withdrawal of the agent may also be performed through bi-caval occlusion techniques in combination with the aortic occlusion device 320. As best viewed in FIG. 17, a doubled-balloon catheter 555 may be employed which is preferably inserted through the femoral vein. The double-balloon catheter 555 includes a pair of balloons 556, 557 each connected to a balloon inflation device (not shown) through suitable lumens in the double-balloon catheter 555. The balloon 556 occludes the superior vena cava 110 and the balloon 557 occludes the inferior vena cava 111. A blood withdrawal lumen in the catheter 555 has an orifice 558 flush with the upper balloon 556 to avoid venous collapse during blood flow into the double-balloon catheter 555. The catheter 555 also has a series of inlet slots 560 for withdrawing blood from the inferior vena cava 111.

Blood drawn into the inlet 558 and slots 560 enters a common lumen and is then directed to the bypass system in the manner described above.

Figure 18:
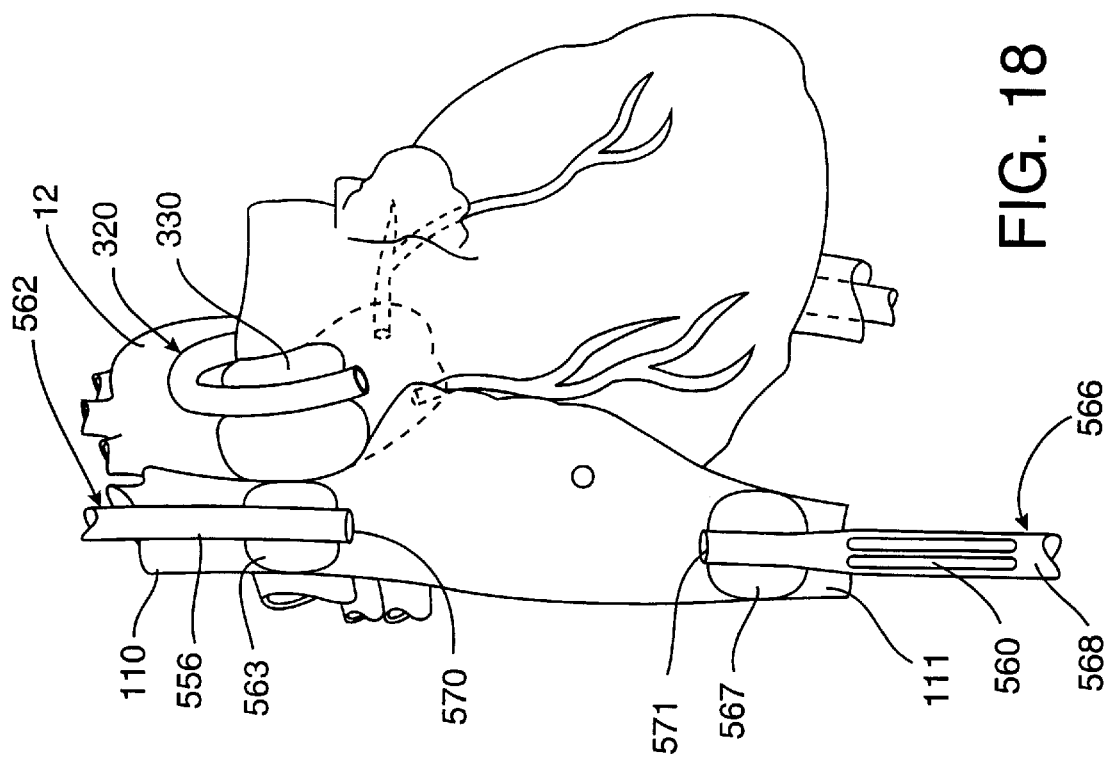
FIG. 18 is an enlarged, fragmentary, top perspective view, in partial cross-section, of a patient's heart with an aortic occlusion device placed in the ascending aorta, and a catheter and a inferior vena cava balloon catheter which collectively isolate the delivered therapeutic agent from systemic circulation.

A separate lumen in the double-balloon catheter 555 opens into the right atrium 45 through aperture 561 to allow evacuation of the agent from the right heart. Bi-caval occlusion is described in commonly owned U.S. Pat. Reissue No. 35,352 to Peters and U.S. Pat. No. 5,584,803, which are hereby incorporated by reference. Bi-caval occlusion may also be performed using two separate balloon catheters. FIG. 18 illustrates occlusion of the superior vena cava 110 with a catheter 562 advanced through the jugular vein 44 and occlusion of the inferior vena cava with a catheter 566.

Figure 19:
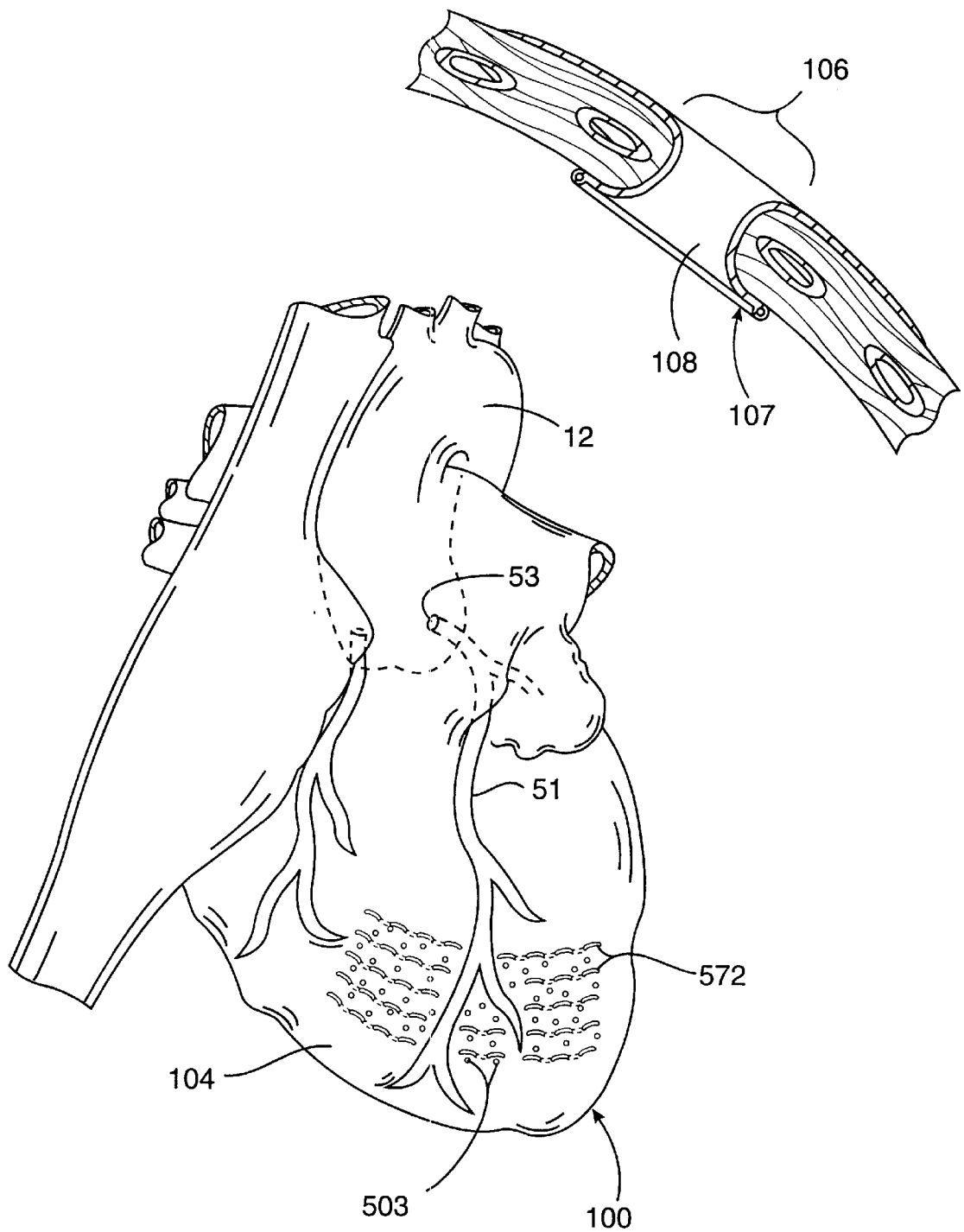
FIG. 19 is a fragmentary, top perspective view of a patient's heart having medicated sutures extending through the myocardium of the heart for timed release of medication impregnated in the suture.
Figure 20:
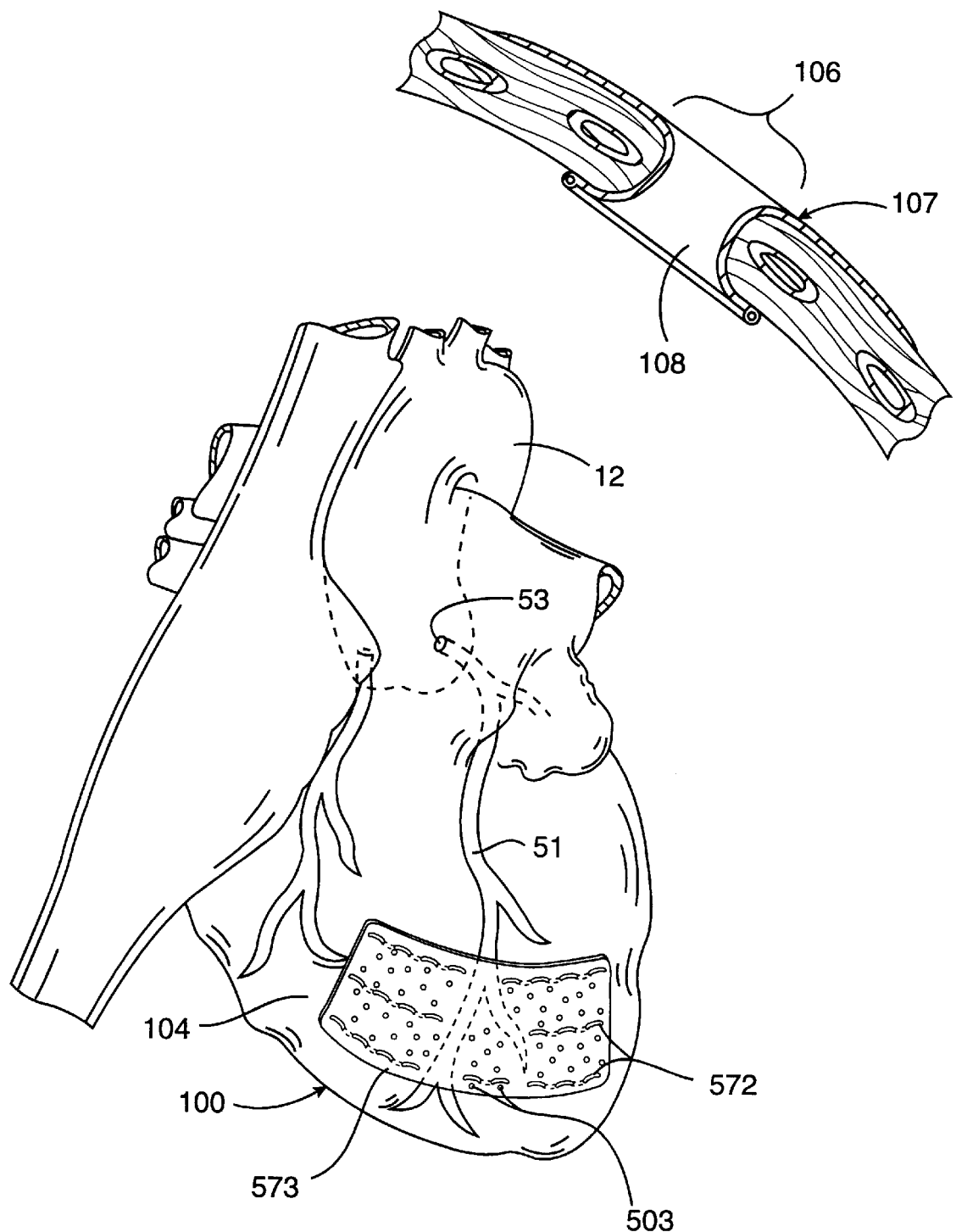
FIG. 20 is a fragmentary, top perspective view of a patient's heart having medicated patch sutured to the myocardium of the heart for timed release of medication impregnated in the suture.

Referring now to FIGS. 19 and 20, an alternative method for delivering a therapeutic agent directly to the epicardial surface 104 of the heart 100 is provided using thoracoscopic techniques. As stated above, timed release of VEGF to a TMR treatment site may have more long term success in stimulating angiogenesis. In contrast, a one dose regimen of VEGF may be absorbed and dissipated too rapidly in the body for effective exposure at the treatment site. One technique to increase the duration of VEGF stimulation is to suspend the VEGF in a substance capable of timed release delivery of the VEGF to the myocardium. Such an extended dosage regimen, accordingly, increases the likelihood of a successful exposure between the VEGF and the TMR treatment site. A topical solution, for example, may be applied directly to the epicardial surface of the heart. This substance may include a fibrin based glue or a biocompatible gel which continuously delivers the VEGF in a timed release manner up to about 25–30 days after the initial application. Alternatively, the VEGF could be encapsulated in a bioabsorbable polymer gel, viscous fluid or mixture of a solid and viscous fluid (slurry) that could release the VEGF over a longer duration of time up to about 2 years. Appropriate polymer gels include absorbable polymers based on polyanhydrides, polycaprolactone, lactide, glycolide, polydioxanone and blends, and copolymers of the former. Topical application of agents, such as VEGF, may also be delivered pericardialy, intramyocardialy, or intrapericardialy.

Initially, TMR could be performed on the heart 100 either endovascularly (FIG. 6) from the endocardium out as mentioned above or from the epicardium inward using lasers introduced percutaneously through an intercostal space 106 (FIGS. 19 and 20). In the latter situation, a small incision 2–3 cm in length may be made between the ribs on the left side of the patient, usually in the third, fourth, or fifth intercostal spaces. When additional maneuvering space is necessary, the intercostal space between the ribs may be widened by spreading of the adjacent ribs, or by removing portions of the ribs to widen the percutaneous penetration. A thoracoscopic access device 107, providing an access port 108, is positioned in the incision to retract away adjacent tissue and protect it from trauma as instruments are introduced into the chest cavity. In other instances, instruments may be introduced directly through small, percutaneous intercostal incisions in the chest.

A laser (not shown) is then introduced to perform TMR on the patient's left ventricle. In accordance with the present invention, an agent delivery applicator (not shown) may then be introduced through access port 108 of access device 107 to apply the suspended VEGF solution directly to the epicardial surface 104 of the left ventricle after a TMR channel 503 is formed. This applicator may be independent from the endoscopic laser or may be integrated or mounted thereto so that the VEGF may be applied immediately after the TMR formed channel 503 is created in the epicardial surface. For example, the endoscopic laser could include a lumen having a delivery port at the distal end of the laser, and a proximal end coupled to a syringe applicator. Manual or powered operation of the syringe applicator could apply the VEGF bioabsorable polymer gel, or the like, directly at or into the TMR created channel.

Another thoracoscopic technique for delivering VEGF to the TMR treated myocardium in a time released delivery manner is through the surgical implantation of a VEGF coated or doped agent delivery material directly in the myocardium. The medication would then be continuously absorbed into the myocardium from the agent delivery material over an extended time. Preferably, the present invention of FIG. 19 provides an agent delivery material mounted to the epicardial surface of the heart with sutures piercing the epicardial surface. These sutures provide a reservoir of agent, as well as a capillary means for delivering the agent directly to the treatment side. Upon implantation of the sutures in myocardium, the agent flows through the suture to be delivered to the myocardium where the tissue contacts the suture. Subsequently, the agent is absorbed and dissipated into the surrounding vascular plexus.

Turning to FIG. 19, sutures 572 are applied to the epicardial surface 104 of heart 100 using thoracoscopic techniques. These suture materials 572 are introduced through access port 108 using thoracoscopic needle drivers, forceps, pliers, or the like, mounted to a curved suture needle (not shown). Applying conventional thoracoscopic surgical skills, the needle can be negotiated through the epicardial surface 104 preferably piercing through the myocardium and tied off on the TMR treated epicardial surface 104 of the heart 100 to implant the suture therein. These sutures 572 are applied either continuously, such as the rows in FIG. 19, or applied in an interrupted fashion. In the preferred form, these sutures are perioperatively coated or saturated with VEGF or are formulated with the VEGF encapsulated in the absorbable polymers composing the suture. Absorbable polymers which may be adequately implanted include polydioxanone, glycolide, lactide, and polycaprolactones to name a few.

Alternatively, as viewed in FIG. 20, a patch 573 containing VEGF is positioned in contact with the epicardial surface 104 of the heart. The patch 573 provides a large reservoir of agent for timed release delivery. Similar to the mounting of the sutures, the patch 573 is mounted to the epicardial surface 104 of the heart 100 through the same thoracoscopic techniques mentioned above. Sutures 572 pierce both the patch 573 and the epicardial surface to provide a capillary means for delivering the agent to the treated myocardial site from the patch 573.

The patch 573 may be applied before the TMR procedure so that the TMR channels 503 are created through the patch 573. It is understood that both the coated or doped sutures or the patch 573 could contain heparin or other anti-clotting agents to prevent or moderate the TMR channels from closing. Suitable agent delivery materials include any biocompatible material capable of absorbing or being doped, loaded, or eluted with a therapeutic agent. Other delivery materials include osmotic transmitters or those capable of leaching or diffusing.

In an alternate mode of operation the aortic occlusion device 10 can be used as a guiding catheter for introducing an endovascular device and for performing an endovascular procedure while the patient is on partial cardiopulmonary support without inflating the occlusion balloon or inducing cardiac arrest. If and when it is desired, the aortic occlusion device 10 can be used to occlude the aorta and arrest the patient's heart thereby converting the patient from partial cardiopulmonary support to full cardiopulmonary bypass. This mode of operation would be advantageous when it is desired to follow the endovascular procedure with another procedure on the heart. For example, when performing a high risk interventional procedure in which complications arise, the patient can be quickly placed on full cardiopulmonary bypass and prepared for surgery without delay.

While the present invention has been described herein in terms of certain preferred embodiments, it will be apparent to one of ordinary skill in the art that modifications and improvements can be made to the invention without departing from the scope thereof.

What is claimed is:

1. A method for delivering a therapeutic agent to the heart of a patient comprising the steps of:

placing an aortic occlusion device in a location within a patient's ascending aorta, the aortic occlusion device having an occluding member and a lumen extending therethrough having an outlet in fluid communication with the patient's ascending aorta;

expanding said occluding member within the patient's ascending aorta to occlude the ascending aorta;

infusing a cardioplegic agent into a coronary vasculature of said patient to arrest the patient's heart;

maintaining circulation of oxygenated blood in the patient while the patient's heart is arrested; and delivering a therapeutic agent into the coronary vasculature through the aortic occlusion device.

2. The method of claim 1 further comprising the step of:

advancing a laser catheter through the aortic occlusion device;

positioning the laser catheter in the patient's heart; and performing a transmyocardial revascularization with the laser catheter.

3. The method of claim 1 wherein,
   said agent includes vascular endothelial growth factors.

4. The method of claim 1 further comprising the step of:
   delivering a stent through the aortic occlusion device.

5. The method of claim 4 wherein,
   the stent includes vascular endothelial growth factors and a fibrin based glue.

6. The method of claim 1 wherein,
   said delivering step is performed by:

passing a distal end of a needle sheath through said lumen of said elongated aortic catheter;

passing a needle of an injection catheter through a lumen of said needle sheath; and piercing the coronary artery wall with the needle upon advancement thereof through an opening in the needle sheath into the coronary artery; and injecting the agent through the needle.

7. The method of claim 1 further comprising the step of:
   occluding the patient's superior vena cava and inferior vena cava to substantially isolate the delivery of the agent to the patient's heart and prevent systemic circulation thereof.

8. The method of claim 1 further comprising the step of:
   withdrawing the agent from the coronary vasculature through a coronary sinus catheter;

occluding the patient's coronary sinus with the coronary sinus catheter.

9. The method of claim 1 wherein said delivering step is performed by:

passing a distal end of a catheter through said lumen of said aortic occlusion device, said catheter having an expandable member at the distal end of thereof, expanding the expandable member to radially expand a flexible infusion array, coupled therearound, against the coronary artery interior wall; and infusing the agent into the coronary artery interior wall through a plurality of orifices in the infusion array while the infusion array remains in contact with the coronary artery interior wall.

* * * * *